United States Patent [19]

Callahan et al.

[11] Patent Number: 5,467,775
[45] Date of Patent: Nov. 21, 1995

[54] MODULAR AUSCULTATION SENSOR AND TELEMETRY SYSTEM

[75] Inventors: Thomas F. Callahan, Maynard; Matthew G. Callahan, Ipswich, both of Mass.

[73] Assignee: University Research Engineers & Associates, Maynard, Mass.

[21] Appl. No.: 405,879

[22] Filed: Mar. 17, 1995

[51] Int. Cl.⁶ ....................................................... A61B 7/04
[52] U.S. Cl. ............................ 128/715; 381/67; 181/131; 181/132; 128/773
[58] Field of Search .................................. 128/715, 773; 181/131, 132; 381/67; D24/134

[56] References Cited

U.S. PATENT DOCUMENTS

| | | |
|---|---|---|
| 1,600,296 | 9/1926 | O'Malley . |
| 3,348,535 | 10/1967 | Gregg ............................ 128/715 |
| 3,938,507 | 2/1976 | Sarnoff et al. . |
| 4,220,160 | 9/1980 | Kimball et al. ................ 128/715 |
| 4,239,189 | 12/1980 | Nelson ............................ 181/131 |
| 4,270,547 | 6/1981 | Steffen et al. .................. 128/671 |
| 4,301,808 | 11/1981 | Taus ................................ 128/687 |
| 4,322,979 | 4/1982 | Fromm ............................ 73/705 |
| 4,436,096 | 3/1984 | Dyck et al. ..................... 128/689 |
| 4,438,772 | 3/1984 | Slavin ............................. 128/715 |
| 4,561,447 | 12/1985 | Kawamura et al. ............ 128/687 |
| 4,594,695 | 6/1986 | Garconnat et al. ............ 367/135 |
| 4,664,127 | 5/1987 | Ikeyama ......................... 128/689 |
| 4,723,555 | 2/1988 | Shue ............................... 128/715 |
| 4,765,321 | 8/1988 | Mohri ............................. 128/715 |
| 4,776,426 | 10/1988 | Kazama ........................... 181/131 |
| 4,777,961 | 10/1988 | Saltzman ........................ 128/715 |
| 4,784,154 | 11/1988 | Shirley et al. ................. 128/715 |
| 4,792,145 | 12/1988 | Eisenberg et al. ............. 128/715 |
| 4,805,633 | 2/1989 | Kotani et al. .................. 128/715 |
| 4,940,023 | 7/1990 | Shue ............................... 128/715 |
| 4,974,601 | 12/1990 | Tranjan et al. ................. 128/696 |
| 4,985,925 | 1/1991 | Langberg et al. ............... 381/72 |
| 5,012,815 | 5/1991 | Bennett, Jr. et al. ......... 128/715 |
| 5,022,402 | 6/1991 | Schieberl et al. .............. 128/671 |
| 5,027,825 | 7/1991 | Phelps, Sr. et al. ........... 128/715 |
| 5,046,103 | 9/1991 | Warnaka et al. ................ 381/71 |
| 5,065,010 | 11/1991 | Knute ............................ 250/227.21 |
| 5,091,954 | 2/1992 | Sasaki et al. ................... 381/72 |
| 5,107,847 | 4/1992 | Knute et al. .................... 128/675 |
| 5,131,047 | 7/1992 | Hashimoto et al. ............. 381/71 |
| 5,134,659 | 7/1992 | Moseley ........................... 381/72 |
| 5,138,663 | 8/1992 | Moseley ........................... 381/71 |
| 5,140,991 | 8/1992 | Niwa ............................... 128/687 |
| 5,181,521 | 1/1993 | Lemelson ....................... 128/736 |
| 5,182,774 | 1/1993 | Bourk ............................. 381/71 |
| 5,213,108 | 5/1993 | Bredesen et al. .............. 128/715 |
| 5,309,922 | 5/1994 | Schechter et al. ............. 128/721 |

Primary Examiner—George Manuel
Assistant Examiner—Kennedy J. Schaetzle
Attorney, Agent, or Firm—Lynn Fiorito Watts

[57] ABSTRACT

A modular auscultation sensor and telemetry system ("MASTS") for sensing body sounds of a patient in a noisy environment where both desired body sounds and undesirable noise may be detected. The MASTS includes a transducer head that comprises two sensors that are substantially acoustically and mechanically isolated from each other. The first sensor is positioned to sense body sounds of a patient when the transducer head is placed against a patient's skin, and the second sensor is positioned to sense primarily noise, if any. The sound signals are transmitted to a digital signal processor carried in a waist-pack or similar container. The digital signal processor processes the sound signals using an adaptive filter scheme to produce an output signal that is indicative of primarily of the body sounds emanating from the patient. A receiving device such as earphones, a hybrid noise reduction ("HNR") headset, an HNR helmet, a tape deck, or a computer may be plugged into the waist-pack and coupled to the digital signal processor to receive the output signals.

45 Claims, 14 Drawing Sheets

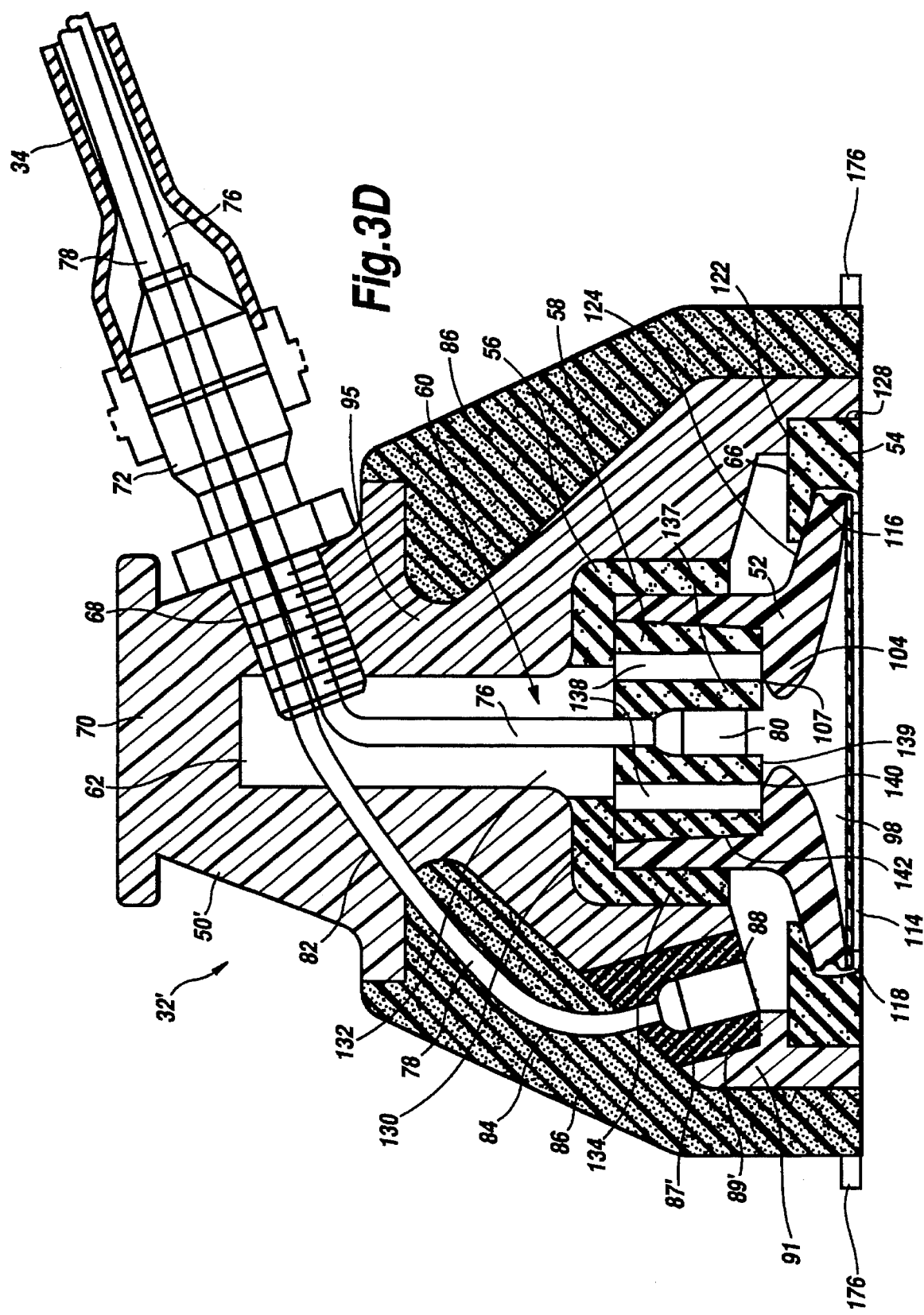

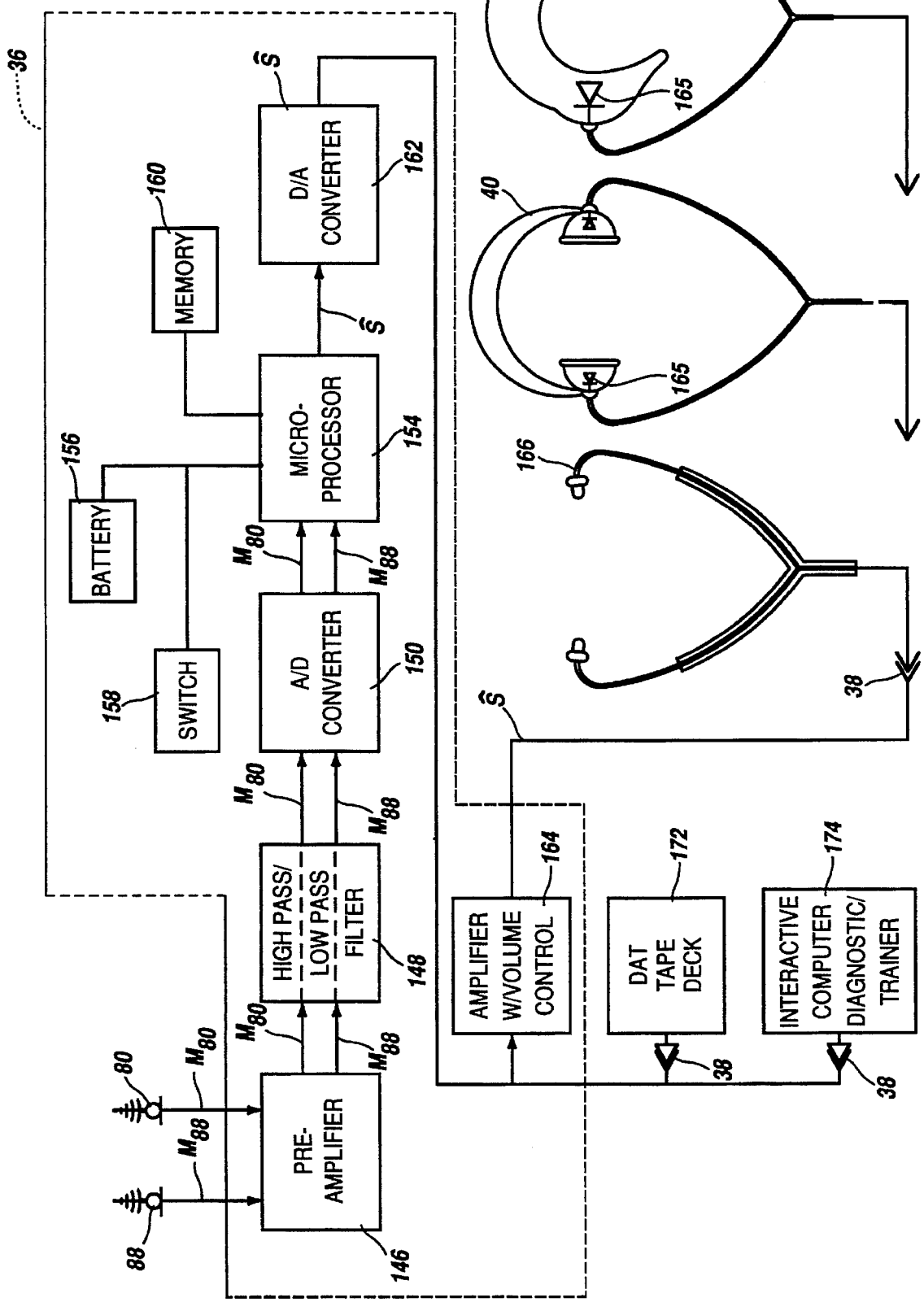

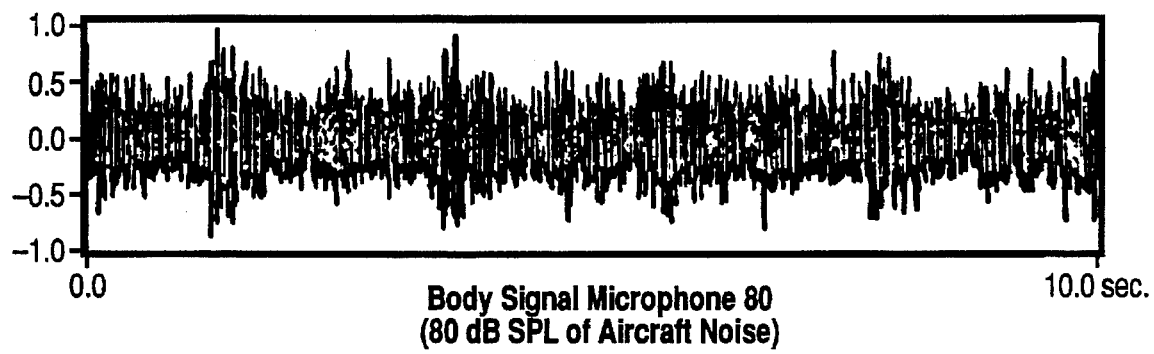
Fig.12A Body Signal Microphone 80 (80 dB SPL of Aircraft Noise)
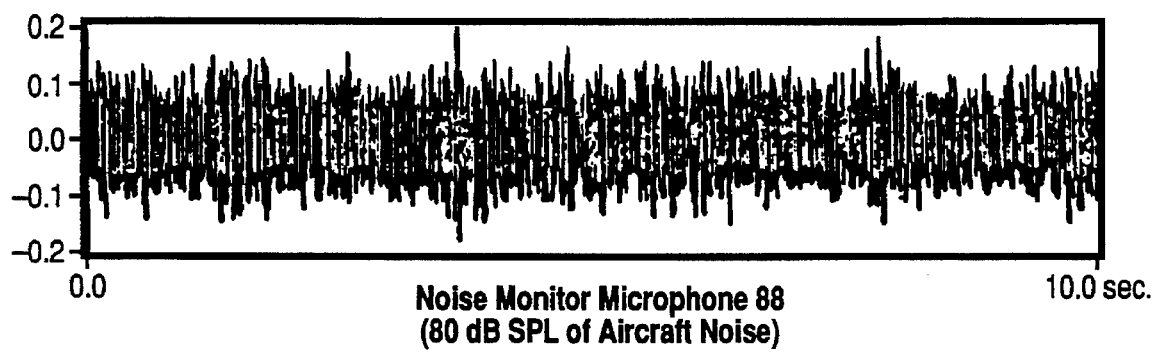
Fig.12B Noise Monitor Microphone 88 (80 dB SPL of Aircraft Noise)
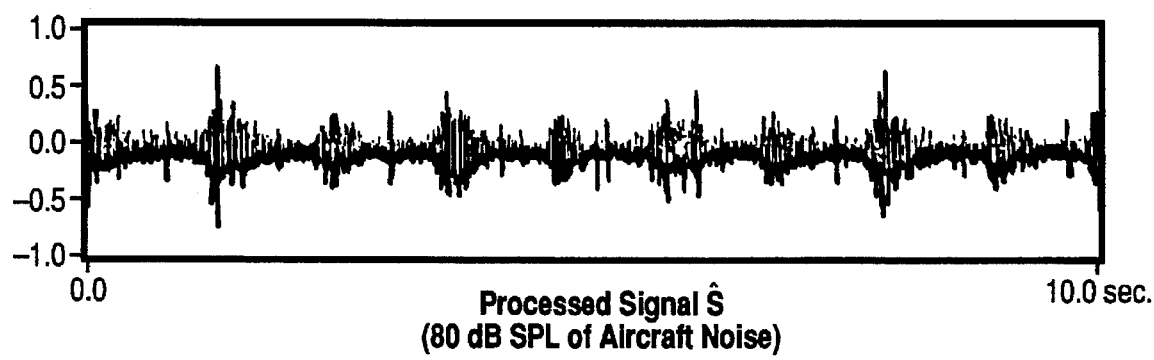
Fig.12C Processed Signal Ŝ (80 dB SPL of Aircraft Noise)

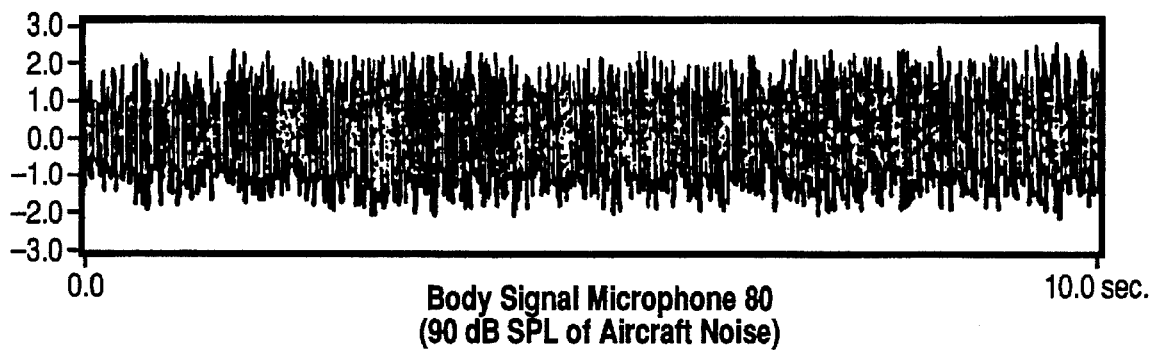
Fig. 13A Body Signal Microphone 80 (90 dB SPL of Aircraft Noise)
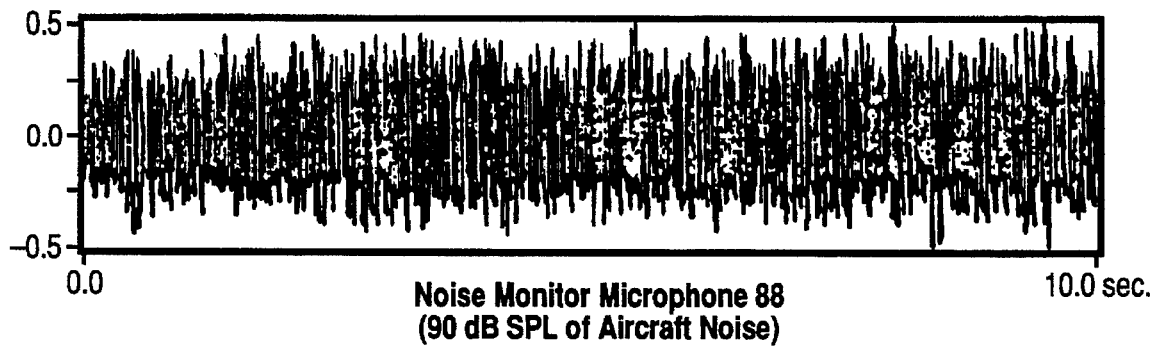
Fig. 13B Noise Monitor Microphone 88 (90 dB SPL of Aircraft Noise)
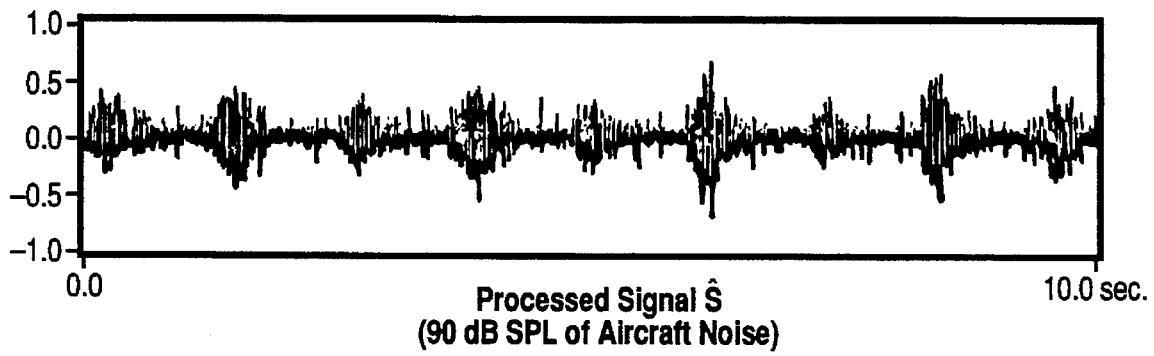
Fig. 13C Processed Signal Ŝ (90 dB SPL of Aircraft Noise)

5,467,775

MODULAR AUSCULTATION SENSOR AND TELEMETRY SYSTEM

BACKGROUND OF THE INVENTION

The present invention was made with U.S. Government support, and the U.S. Government has certain rights in the invention.

The present invention relates to an improved auscultation sensor and telemetry system that can be used in any type of sound environment to auscultate patient body sounds. In particular, the present invention relates to a modular auscultation sensor and telemetry system that comprises several interacting modules.

Auscultation involves the listening of body sounds such as, for example, cardiac, pulmonary, and Korotkoff (blood pressure) sounds. In a noisy environment, however, auscultation of such sounds can be exceedingly difficult if not impossible with current state-of-the-art stethoscopes.

FIG. 1 illustrates an example of a state-of-the-art, mechanical type, stethoscope 10 typically used to listen to the body sounds of a patient. The state-of-the-art stethoscope 10 essentially comprises a bell-shaped acoustic coupler 12 that is placed in contact with the skin surface 14 of a patient in, for example, the thorax region, in order to detect body sound signals S that are broadcast through the skin surface 14. Stretched across the bottom of the acoustic coupler 12 is a diaphragm or membrane 16 that aids in transmitting the sound signals S to the interior 17 of the acoustic coupler 12. Coupled to the interior 17 of the acoustic coupler 12 is a hollow, air-filled transmission tube 18 which transmits the sound signals to a pair of spring-loaded, air-filled, metal tubes 19. Attached to the ends of each of the metal tubes 19 are ear canal adapters 20 that can be positioned in the ear canals of a user. The acoustic coupler 12 in combination with the diaphragm or membrane 16, the transmission tube 18, metal tubes 19, and ear canal adapters 20, collectively function as a mechanical microphone or transducer, an amplifier, and sound transmitter. For example, the coupler 12 detects the signals S that are broadcast through the skin surface 14 and amplifies the signals, the transmission tubes 18 and 19 mechanically transmit the signals via a column of air within the tubes 18 and 19 to the ear canal adapters 20, and the adapters 20 emit a sound signal to the listener.

In addition to detecting the desired body signals S, the stethoscope 10 will also detect airborne noise $N_A$ and surface motion noise $N_S$, that can occur when the coupler 12 moves along the thorax surface 14. Furthermore, sounds coming from the body may also include unwanted noise $N_B$, for example, sounds produced when the patient moves his or her muscles or ambient sounds that are transmitted through the patient to the stethoscope 10.

The airborne noise $N_A$, surface motion noise $N_S$, and body noise $N_B$ can be much louder than the body signals S. For example, in ambulances and various aircraft used to transport critically ill or seriously injured patients the sound pressure levels, measured in decibels (dBs), may be in the range of 80 to 120 dBs. In particular, the sound level can be in the range of 90 to 100 dBs in a civil helicopter, 90 to 120 dBs in a military helicopter, and 80 to 85 dBs in an ambulance. The intensity of breath sounds of a healthy adult, however, is approximately in the 22 to 30 dB range. In such an environment it would generally be impossible to hear the breath sounds of a patient with a typical state-of-the-art stethoscope.

Some state-of-the-art stethoscopes may include two transmission tubes constructed from a polyvinylchloride material. In addition, the ear canal adapters of some state-of-the-art stethoscopes have been modified to form an improved audio seal with the ear canal in order to eliminate some ambient noise that the user may directly hear. Still other state-of-the-art stethoscopes may employ a small battery-operated, electronic amplifier in the transmission tube in order to amplify the signals detected by the stethoscope. The amplifier, however, increases the level of all sounds detected by the stethoscope including airborne noise $N_A$, surface motion noise $N_S$, and body noise $N_B$. In general, the sensitivity of the state-or-the-art stethoscopes, including those with battery-operated amplifiers, are considered to be inadequate, particularly in a noisy environment.

The present invention, therefore, seeks to provide an effective auscultation system that optimizes the signal to noise (S/N) ratio by decreasing the level of the noise N reaching the listener's ears.

SUMMARY OF THE INVENTION

The present invention provides a modular auscultation sensor and telemetry system ("MASTS") for sensing body sounds of a patient in a noisy environment where both desired body sounds and undesirable noise may be detected. The MASTS includes a transducer head having a first chamber and a second chamber substantially acoustically isolated from the first chamber. Two embodiments of the transducer head are provided. In both embodiments, the transducer head comprises an outer housing and an inner housing having an inner chamber that defines the first chamber. The inner housing also has an outer opening connecting to the inner chamber that is covered by a diaphragm. In the first embodiment, the second chamber is defined by a substantially tubular isolator that is positioned in a channel provided in the outer housing. In the second embodiment, the second chamber is defined by a chamber formed between the inner and outer housings.

The transducer head of both embodiments further comprises a first sensor positioned in or adjacent to the first chamber in order to sense sounds within the first chamber and a second sensor positioned in or adjacent to the second chamber in order to sense sounds within the second chamber. A telemetry conduit is coupled to the transducer head and includes a first signal conductor operably coupled to the first sensor and a second signal conductor operably coupled to the second sensor.

A digital signal processor is coupled to the first and second signal conductors to receive the sound signals from the first and second sensors. The digital signal processor processes the sound signals to produce an output signal that is indicative of the body sounds emanating from the patient. A receiver coupled to the digital signal processor receives the output signal from the digital signal processor.

The body sounds of a patient are sensed by placing the diaphragm against the skin surface of a patient so that the desirable body sounds emanating from the patient may enter the first chamber through the outer opening and be sensed by the first sensor. Undesirable noise, if any, may also enter the first chamber. Primarily undesirable noise, however, and not the desirable body sounds, enters the second chamber and is sensed by the second sensor.

The digital signal processor then processes the sound signals from the first and second sensors and extracts an output signal that is indicative primarily of the body sounds emanating from the patient. The digital signal processor includes an adaptive filter that processes and conditions samples of the sound signals from the second sensor and generates a filtered signal. A digital subtractor forming part of the digital signal processor board subtracts the filtered signal from the sound signal from the first sensor and generates the output signal that is indicative of the desired body signal. Samples of the output signal are fed back to the adaptive filter to dynamically adjust the filter.

BRIEF DESCRIPTION OF THE DRAWINGS

The above and other objects and advantages of the invention will become apparent from consideration of the following detailed description when read in conjunction with the accompanying drawings, in which like reference characters refer to like parts throughout. The terms "upper", "lower", "top" and "bottom" may be used throughout the specification for purposes of clarity and convenience in describing the invention. The use of such terms is not intended to be limiting with regard to any particular orientation of the device.

FIG. 3D is a partial side cross-section view of a second embodiment of the ASTD, wherein the transducer and part of the telemetry conduit are shown;

FIG. 10 is a block diagram of the modular auscultation sensor and telemetry system ("MASTS") in accordance with the present invention;

FIGS. 12A, 12B and 12C are plots illustrating test results obtained using the ASTD of FIG. 3D in an environment where the average sound pressure level was 80 dB SPL, wherein FIG. 12A is a plot of a body signal detected by the body signal microphone over a period of 10 seconds, FIG. 12B is a plot of a noise signal detected by the noise monitor microphone over the period of 10 seconds, and FIG. 12C is a plot of a processed signal $\hat{S}$ obtained by processing the signals from the body signal microphone and noise monitor microphone in accordance with the present invention over the period of 10 seconds;

FIGS. 13A, 13B and 13C are plots illustrating test results obtained using the ASTD of FIG. 3D in environment where the average sound pressure level was 90 dB SPL, wherein FIG. 13A is a plot of a body signal detected by the body signal microphone over a period of 10 seconds, FIG. 13B is a plot of a noise signal detected by the noise monitor microphone over the period of 10 seconds, and FIG. 13C is a plot of a processed signal $\hat{S}$ obtained by processing the signals from the body signal microphone and noise monitor microphone in accordance with the present invention over the period of 10 seconds; and FIGS. 14A, 14B and 14C are plots illustrating test results obtained using the ASTD of FIG. 3D in environment where the average sound pressure level was 100 dB SPL, wherein FIG. 14A is a plot of a body signal detected by the body signal microphone over a period of 10 seconds, FIG. 14B is a plot of a noise signal detected by the noise monitor microphone over the period of 10 seconds, and FIG. 14C is a plot of a processed signal $\hat{S}$ obtained by processing the signals from the body signal microphone and noise monitor microphone in accordance with the present invention over the period of 10 seconds.

DETAILED DESCRIPTION OF THE INVENTION

Figure 1:
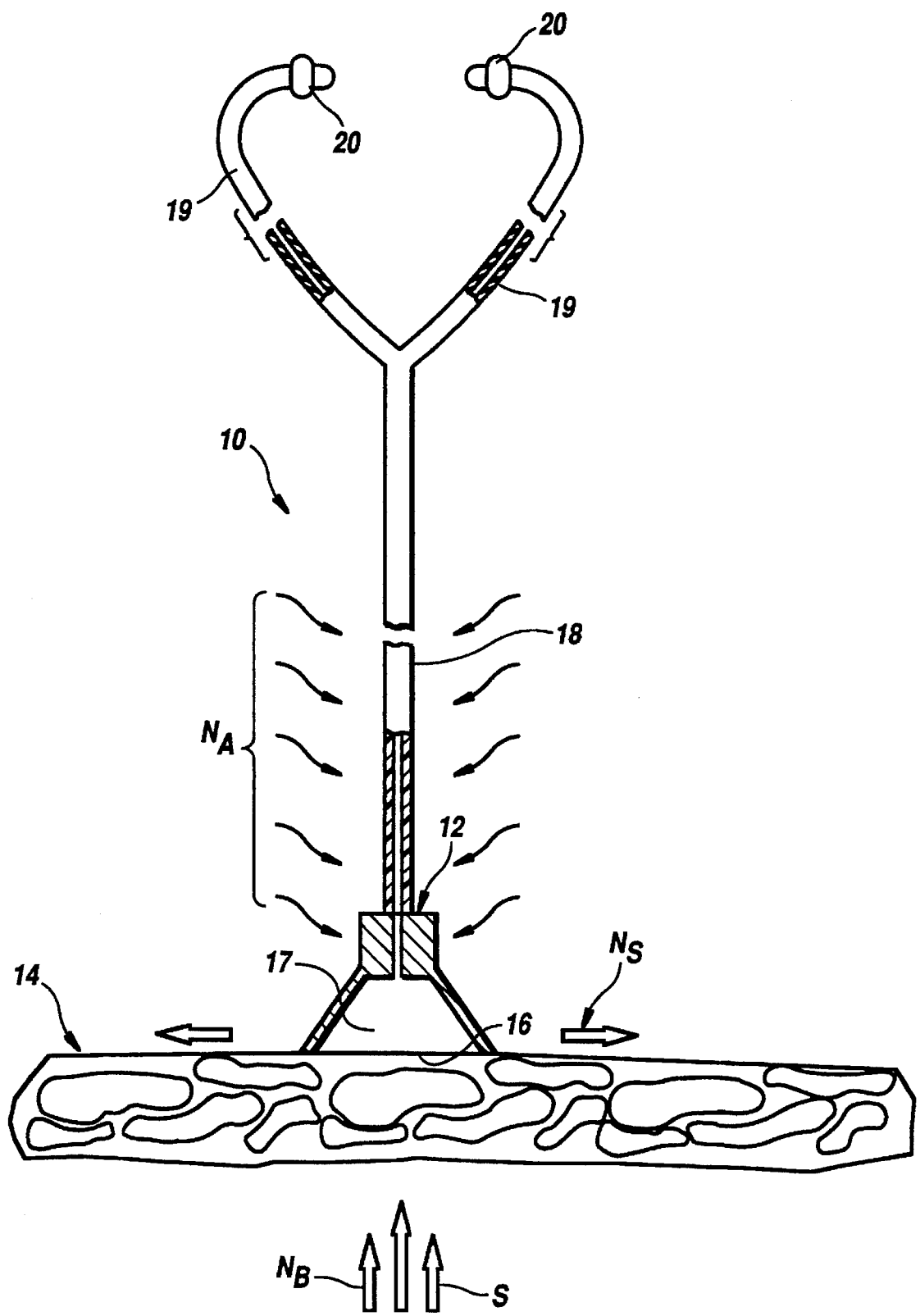
FIG. 1 is a partial cross-sectional side view of a prior art stethoscope positioned on the skin surface of a patient.
Figure 2:
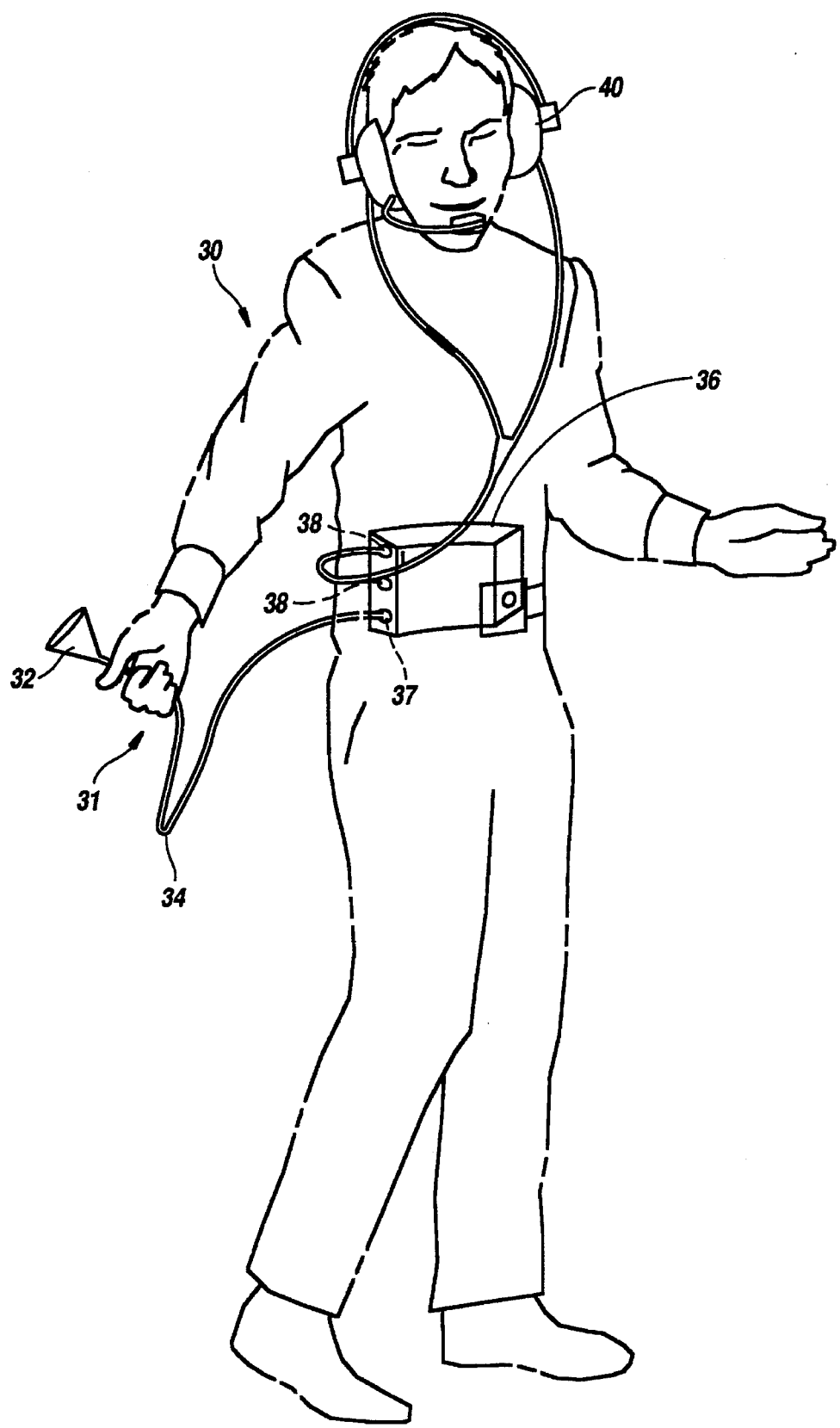
FIG. 2 is a perspective view of an individual using an embodiment of the modular auscultation sensor and telemetry system ("MASTS") of the present invention.

The present invention provides a modular auscultation sensor and telemetry system (hereinafter referred to "MASTS") that includes a plurality of modules which in combination detect and transmit to a user's ears various body sounds such as cardiac, pulmonary, and Korotkoff (blood pressure) sounds in a noisy environment. FIG. 2 illustrates an individual 30 using an embodiment of the MASTS. The MASTS includes a module referred to as an auscultation sensor and telemetry device ("ASTD") 31 that comprises a sensor or transducer 32, that may be placed against the skin wall of a patient to detect the patient's body signals S, and a telemetry conduit 34. In a noisy environment, the transducer 32 may also detect noise N that may include airborne noise $N_A$, surface motion noise $N_S$, as well as body noise $N_B$.

The transducer 32 is electrically coupled to an electronic signal processing unit and amplifier (not shown in FIG. 2) by conductors (also not shown in FIG. 2) encased within a protective sheath of the telemetry conduit 34. The telemetry conduit 34 via the conductors, carries an electrical analog of the detected body signals S and noise N to a pack or container 36 that may be worn around the waist of the user 30. As explained in further detail below with reference to FIG. 10, the pack 36 carries an electronic signal processing unit, an amplifier, a power supply and other electronic hardware for processing the incoming raw signals so that the noise N is essentially removed or cancelled and an output signal indicative of the desired body sound is generated.

The waist-pack 36 is provided with input and output receptacles 37 and 38 for interconnecting the electronic hardware in the pack 36 with external modules or devices. For example, the ASTD 31 may be connected to the input receptacle 37. A module such as a headset 40 or other listening or speaker device may be connected to the output receptacles 38. (FIG. 10 illustrates various examples of speaker devices 40, 166, and 170.) As discussed further below, the output receptacles 38 may also be connected to other external modules or receiver devices such as a tape recorder, computer, telephone or other communication plug. Although the pack 36 is illustrated as one that can be worn around the waist of the user 30, a different shaped pack that can be worn or supported elsewhere may be employed. Furthermore, more or fewer receptacles 37 and 38 or different type receptacles can be provided.

The MASTS includes a headset module 40 or other speaker module that may be plugged into one of the receptacles 38 of the pack in order to receive the processed signals from the electronic hardware and broadcast the signals to the user 30. Preferably, the headset 40 is a hybrid noise reduction (HNR) headset which both actively and passively reduces the noise level that may directly reach the user's ear. Other types of listening devices may include an HNR helmet or ear phones which comprise ear plugs with internal speakers. An example of an acceptable HNR headset is a Noise Guard Model HMEC 200 made by Sennheiser Electronics, KG, or an ANR Headset System, Model No. 70800-100 made by Telex Communications, Inc. of Minneapolis, Minn. The headset technology can also be employed in an HNR helmet.

FIGS. 3A, 3B, 4 and 5A illustrate a first preferred embodiment of the transducer 32 and the telemetry conduit 34. The transducer 32 comprises an outer transducer housing 50 and an inner transducer housing 52 suspended from the outer housing 50 by several elastomer isolators 54, 56, and 58 so that the inner housing 52 is significantly isolated both mechanically and acoustically from the outer housing 50. Preferably, the inner and outer housings 50 and 52 are molded from an engineering grade plastic such as rigid foam polyurethane, but may also be made from aluminum or other suitable materials. The rigid foam plastic, however, is preferable due to its better sound isolating properties and comparably lower ability to transmit sound.

Figure 5A:
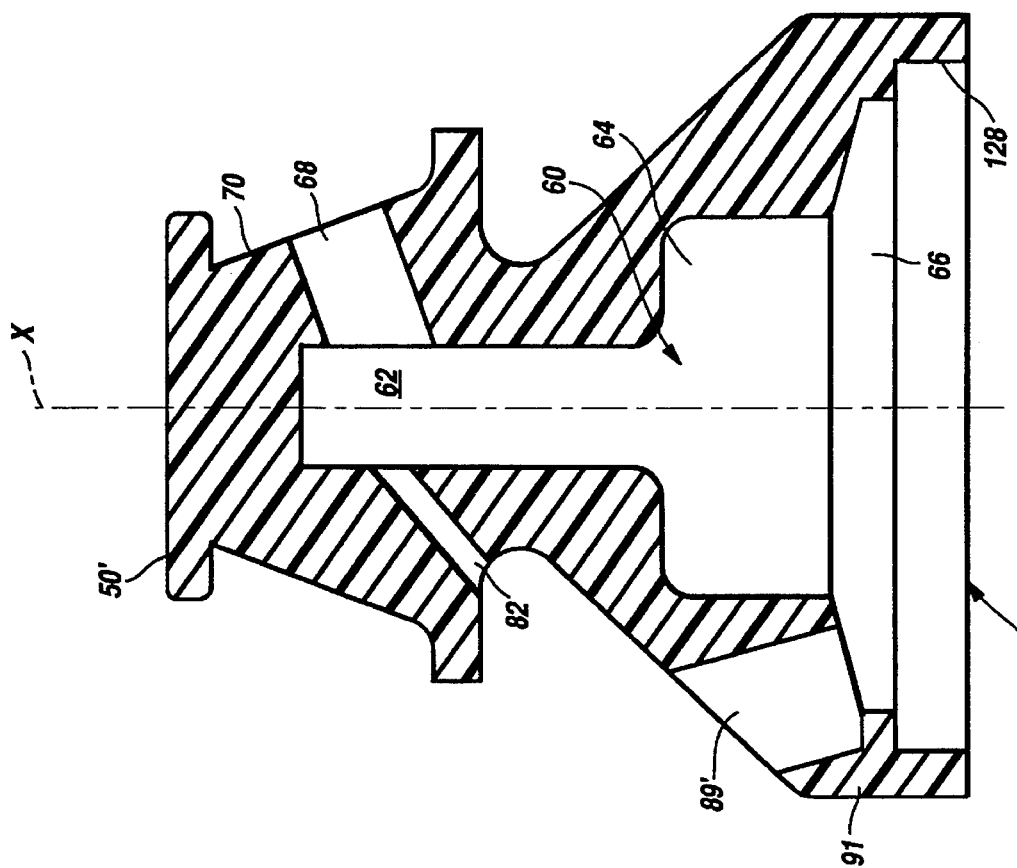
FIG. 5A is a side cross-sectional view of the outer housing of the transducer of FIG. 3A.

With reference to FIG. 5A, the outer transducer housing 50 has a generally bell-shaped configuration and is substantially symmetrical about a central longitudinal axis X with the exception of three channels (68, 82, 89) discussed further below. The outer housing 50 has an interior cavity 60 and bottom opening 61. The interior cavity 60 has three primary subchambers, upper subchamber 62, middle subchamber 64, and lower subchamber 66, each with a different outer diameter. A channel 68 passes through the side of the upper portion 70 of the outer housing 50, connecting the interior cavity 60 with the exterior.

Figure 3A:
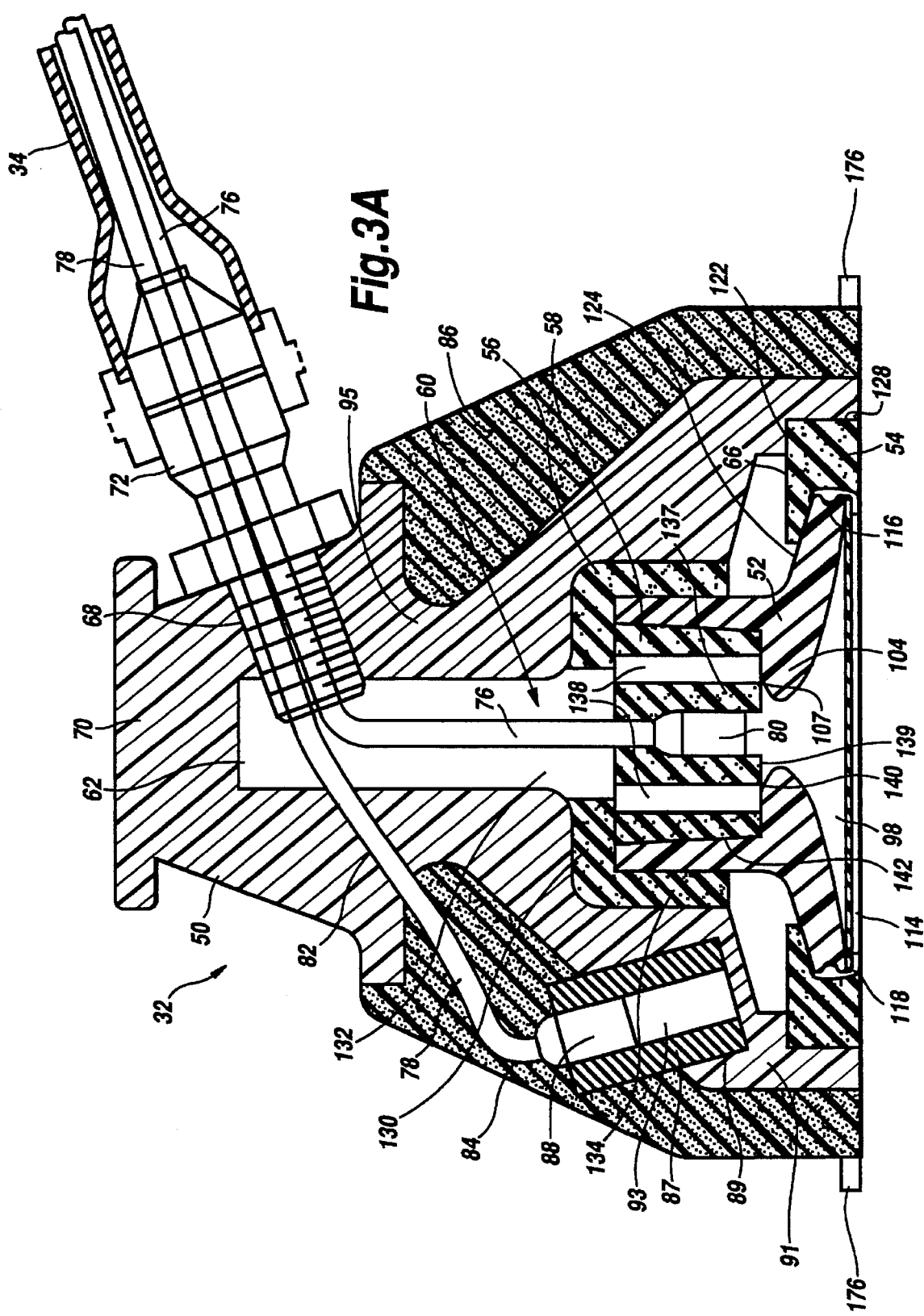
FIG. 3A is a partial side cross-sectional view of a first embodiment of the auscultation sensor and telemetry device ("ASTD") that forms part of the MASTS of FIG. 2, wherein the transducer and part of the telemetry conduit are shown.
Figure 3B:
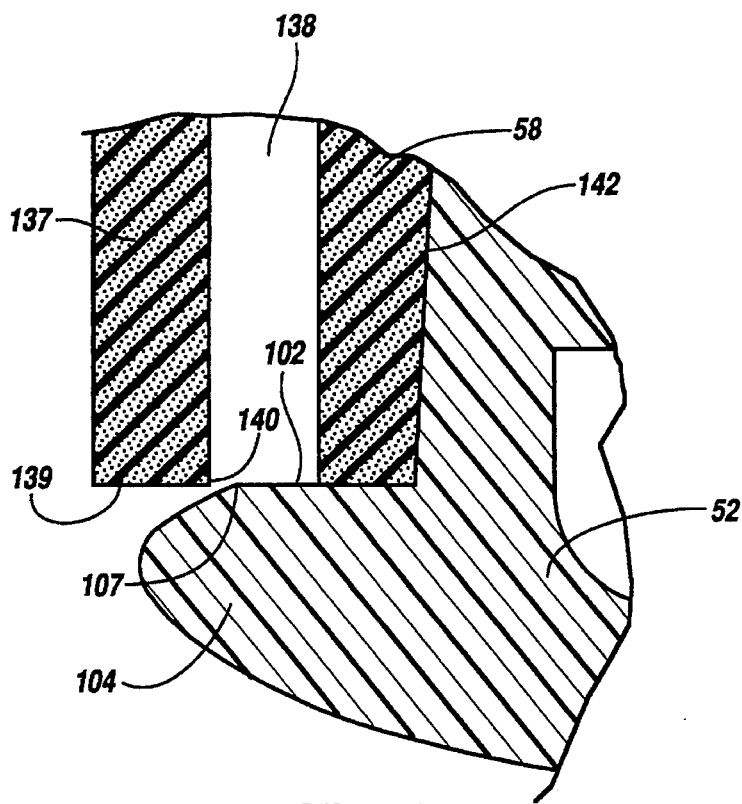
FIG. 3B is an enlarged view of a section of the transducer of FIG. 3A.

As shown in FIG. 3A, a soft tube fitting 72, that is coupled to the telemetry conduit 34, is mechanically received in the channel 68. The channel 68 and fitting 72 may be provided with complementing threads in order to establish the mechanical connection. The fitting 72 has an interior passageway through which two electrical conductors 76 and 78 pass. These conductors carry electrical signals to the electronic hardware in the waist pack 36. Although the conductors 76 and 78 are described as electrical conductors, they may alternatively be optical conductors. Furthermore, although the channel 68 is shown extending through the side of the upper portion 70 of the outer housing 50, the channel 68 may alternatively extend through the top of the outer seal 50.

The first electrical conductor 76 is directed down through the upper subchamber 62 of the outer housing to the middle subchamber 64. Mounted to the end of the first conductor 76 is an electro-acoustic body signal transducer 80. The electro-acoustic body signal transducer 80 is preferably a state-of-the-art miniature microphone that is positioned to sense sound signals emanating from the patient's body and convert the sounds into electrical impulses. Preferably, the microphone is a back electret type condenser microphone that is commercially available from such electronics suppliers as Telex Communications, Inc. and Radio Shack. An example of an acceptable miniature microphone is a Model ELM 22 System made by Telex Communications, Inc. The condenser microphone preferably has generally flat response characteristics over the frequency range of interest and a preferred dynamic range of 90 dBs. As discussed in more detail below, the body signal transducer or microphone 80 is held in position by the third elastomer isolator 58.

The second electrical conductor 78 is directed across the upper subchamber 62 and through a second channel 82 provided in the opposing side of the upper portion 70 of the outer housing 50. The second electrical conductor 78 then extends through a passageway 84 provided in a passive noise reduction shield 86 and into a channel 89 located in a lower portion 91 of the outer housing 50. Unlike the channels 68 and 82 which are through holes, the channel 89 is preferably a blind hole that does not extend all the way through the outer housing 50 and has an opening at one end. Mounted to the end of the second electrical conductor 78 is a noise monitor transducer 88. The noise monitor transducer 88 is preferably a state-of-the-art miniature microphone that is positioned to sense ambient noise $N_A$ which may be transmitted into the transducer 32 and convert the noise into electrical impulses. Preferably, the microphone is a back electret type condenser microphone that is commercially available from such electronics suppliers as Telex Communications, Inc. and Radio Shack. An example of an acceptable miniature microphone is a Model ELM 22 System made by Telex Communications, Inc. The condenser microphone preferably has generally flat response characteristics over the frequency range of interest and a preferred dynamic range of 90 dBs.

As explained in more detail below, the body signal microphone 80 and noise monitor microphone 88 are mounted within the transducer 32 so that they are substantially acoustically and mechanically isolated from one another.

The noise monitor microphone 88 is held in the third channel 89 by a fourth elastomer isolator 87. The fourth elastomer isolator 87 is generally tubular in shape with a central passageway having openings at either end. The isolator 87 is positioned in the third channel 89 so that the opening at one end of the central passageway is covered by a portion of the outer housing 50. The opening at the opposing end is covered or plugged by the noise monitor microphone 88 which is preferably positioned at least partially into the central passageway so that an air chamber 93 is formed between the noise monitor microphone 88, the inner walls of the isolator 87, and the portion of the outer housing 50 that covers the first or lower opening.

The fourth elastomer isolator 87 is preferably made from an elastomer material with a greater than 50 Shore durometer. A relatively soft elastomer material is desirable in order to provide a significant mechanical and acoustical impedance differential between the rigid outer housing 50 and the outer shell of the noise monitor transducer 88. This minimizes the amount of noise conducted from the outer housing 50 to the noise monitor transducer 88 that may be originally conducted through the outer elastomer foam shield 86 of the transducer 32. The fourth elastomer isolator 87, however, must also be structurally stable enough to hold the noise monitor microphone 88 in place. Additional structural stability may be provided by containing the fourth elastomer isolator in a thin-walled cylinder made from aluminum, plastic, or the like. With the noise monitor microphone so positioned, it will primarily detect sound waves in the air chamber 93.

Although the blind hole or channel 89 is shown positioned near the lower portion 91 of the outer housing 50, it could be located in other portions of the outer housing 50. For example, the blind hole or channel 89 could be positioned closer to the upper end 70 of the outer housing as represented by reference numeral 95. Furthermore, the blind hole or channel 89 could extend at a different angle than that shown in FIGS. 3A and 5A. For example, instead of more vertical orientation, the blind hole or channel 89 could have a more horizontal orientation. The particular desired location and orientation of the blind hole 89 would depend on the degree of acoustical and mechanical isolation desired between the first and second microphones 80 and 88.

In the embodiment shown in FIG. 3A, the fourth elastomer isolator 87 is greater in length than the channel 89 is in depth so that the isolator 87 partially protrudes from the channel 89. Alternatively, however, depending upon the location and orientation of the channel 89, the channel 89 can have a depth that is equal to or more than the length of the isolator 87. In that case, the isolator 87 would not need to be as structurally stable and can be made from an elastomer material that is less rigid.

Figure 6:
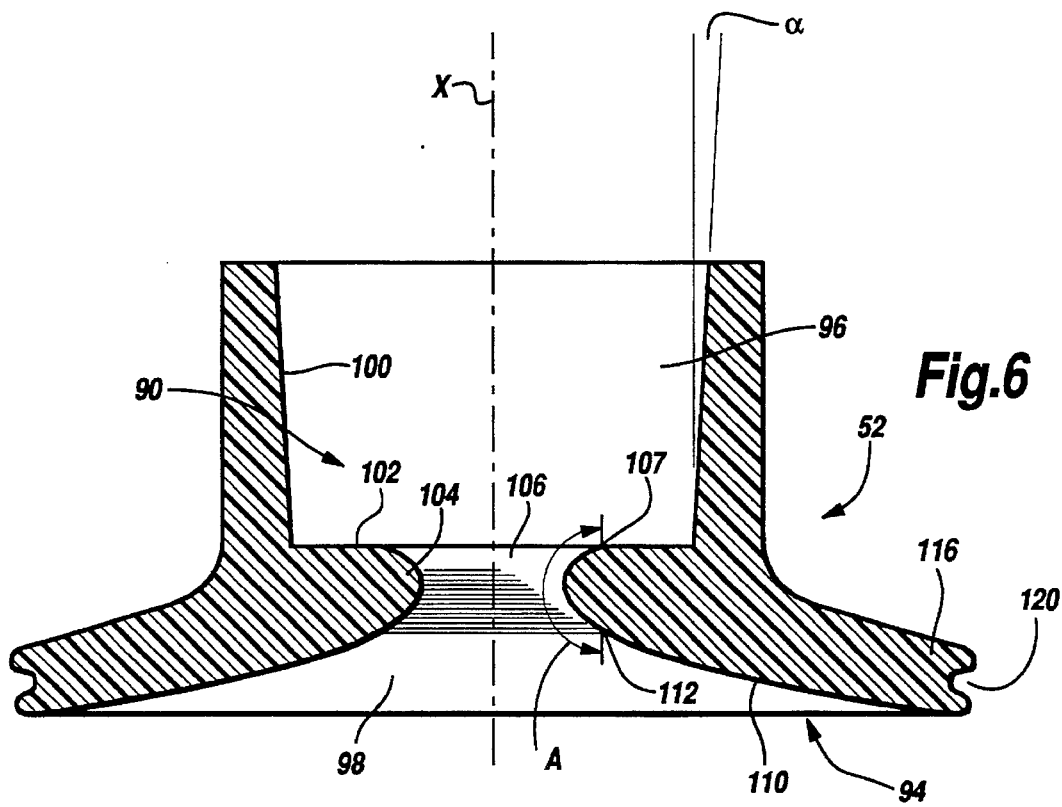
FIG. 6 is a side cross-sectional view of the inner housing of the transducer of FIG. 3A.
Figure 7:
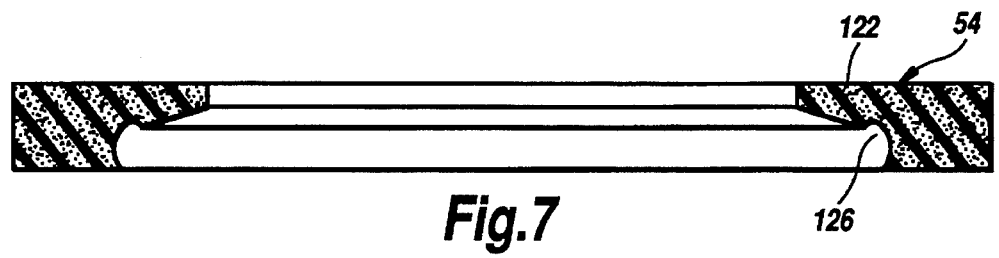
FIG. 7 is an enlarged cross-sectional view of the first elastomer isolator of the transducer, which assists in isolating the inner housing from the outer housing.

With reference to FIG. 6, the inner transducer housing 52 also has a generally bell-shaped configuration that is substantially symmetrical about a central longitudinal axis X. The inner transducer housing 52 has an interior cavity or chamber 90 and both a top opening 92 and a bottom opening 94. The interior cavity or chamber 90 is divided generally into an upper subchamber 96 and a lower subchamber 98. The upper subchamber 96 is defined by a circumferential side wall 100 which preferably has an approximately three degree internal draft or taper $\alpha$ so that the diameter of the subchamber 96 increases towards the top opening 92. The upper subchamber 96 is also partially bounded by a lower wall 102 that is defined by an inwardly-extending projection 104 of the inner housing 52.

The projection 104 extends about the entire inner circumference of the inner housing 52 and projects inwardly only partially so that an opening 106 is defined between the upper and lower subchambers 96 and 98. The projection 104 has a substantially flat upper surface that defines the bottom wall 102 of the upper subchamber 96. From the edge 107 of the bottom wall 102, the projection 104 curves smoothly about a radial arc A where it connects with the inner surface 110 of the lower subchamber 98. From the intersection 112 of the radial arc A and the inner surface 110, the inner surface 110 generally follows the contour of a segment of an inverse paraboloid.

Under normal conditions, a sound wave moving parallel to the axis of symmetry of a paraboloid will be reflected from the surface toward the focal point. This type of design mechanically amplifies the reflected sound. An inverse paraboloid, however, has a tendency to minimize signal distortion. The body signal microphone 80 is preferably aligned with the axis of symmetry of the inverse paraboloid.

Figure 9:
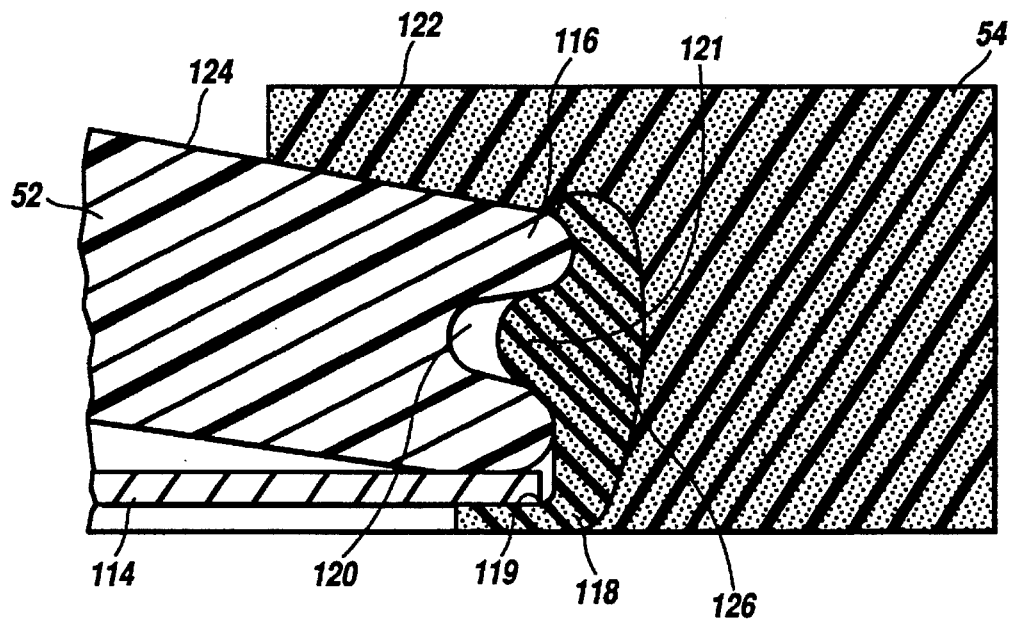
FIG. 9 is a partial side cross-sectional view of a portion of the transducer illustrating the structural arrangement of the lower end of the transducer.

Referring back to FIG. 3A, a diaphragm 114 extends across the bottom opening 94 of the inner housing 52. The diaphragm 114 is a state-of-the-art thin plastic membrane which is sensitive to sound and is durable. The purpose, however, of the diaphragm 114 is primarily to prevent matter from entering the lower subchamber 98 of the transducer 32. The outer edges of the diaphragm 114 are held against the lower outer edge 116 of the inner housing 52 in a conventional manner by a bezel 118 made from an elastomer material. FIG. 9 more clearly shows the bezel connection. The bezel 118 is in the shape of a ring having a lower lip 119 that holds the diaphragm against the lower surface of the inner housing 52. The lower outer edge 116 of the inner housing 52 is provided with a groove 120 that extends about the outer circumference of the inner housing 52 and receives a protruding portion 121 of the bezel 118 that is inserted into the groove 120. The bezel 118 has a diameter that is slightly smaller that the diameter of the inner housing 52 at the groove 120. To position the bezel 118, therefore, it is stretched over the lower edge of the inner housing 52 and released so that the protruding portion 121 snaps into the groove 120 and the lip 119 holds the diaphragm 114.

Alternatively, the diaphragm 114 may be held in position using a second conventional configuration (not shown). In the second configuration, the bezel is made of a rigid material and is provided with a female mechanical thread, and the lower outer edge 116 of the inner housing 52 is provided with a mating male mechanical thread. The diaphragm 114 is, therefore, held in place when the bezel 118 is threaded onto the lower outer edge 116 of the inner housing 52. Other suitable conventional means for holding the diaphragm in place may also be used.

The lower subchamber 98 of the inner housing 52 and the diaphragm 114 are designed to closely approximate the configuration of a state-of-the-art stethoscope so that the mechanical impedance closely matches the mechanical impedance of a state-of-the-art stethoscope and the resulting modulated sound character will, therefore, be that which medical personnel are accustomed to hearing.

As mentioned above, the inner housing 52 is suspended (mechanically and acoustically isolated) from the outer housing 50 by three elastomer isolators 54, 56, and 58. With reference to FIGS. 3A, 3B, 4, 7 and 9, the lower end of the inner housing 52 is held in place by the first elastomer isolator 54. The first elastomer isolator 54 is an annulus or collar that fits about the lower outer edge 116 of the inner housing 52. The first isolator 54 has a lip portion 122 that extends over the upper surface 124 of the inner housing 52 and has an inner groove 126 that surrounds the bezel 118. The first elastomer isolator 54 fits within a counter bore 128 provided in the lower subchamber 66 of the outer housing 50. Preferably, the first isolator 54 is slightly compressed and cemented in place in order to obtain a good air seal.

The upper end of the inner housing 52 is held in place by the second and third elastomer isolators 56 and 58, respectively. The second elastomer isolator 56 is in the shape of a collar having an upper wall 130 with an opening 132 and a side wall 134. The second isolator 56 is pressed into the middle subchamber 64 of the outer housing 50 and is fitted over the top of the inner housing 52. When so positioned, the isolator's upper wall 130 is squeezed between the upper edge of the inner housing 52 and the upper wall of the middle subchamber 64, and the isolator's side wall 134 is squeezed between the side wall 100 of the inner housing 52 and the side wall of the middle subchamber 64.

Figure 8:
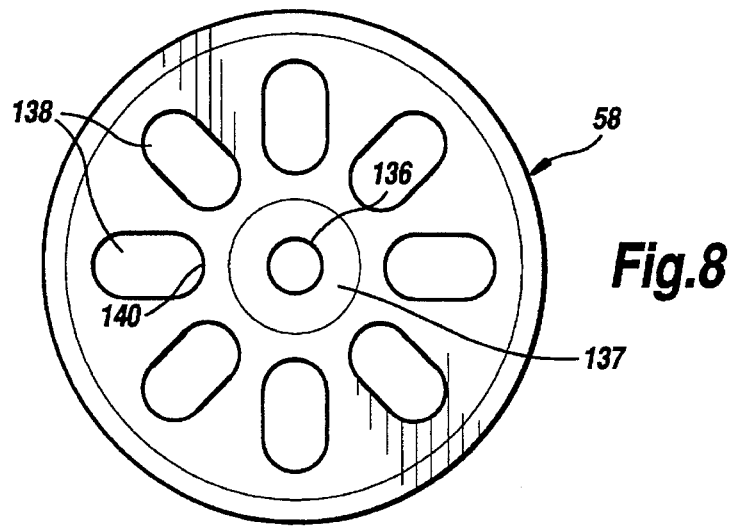
FIG. 8 is a top view of the fourth isolator of the transducer, that isolates the body signal microphone from the inner housing.

The third elastomer isolator 58 fits within the upper subchamber 96 of the inner housing 52 supports the body signal microphone 80. With reference to FIG. 8, the third elastomer isolator 58 has a generally wheel-like configuration. In particular, the isolator 58 has a central through-hole 136 in which the body signal microphone 80 is positioned (see FIG. 3A). The shape of the through-hole 136 closely follows the outer contour of the microphone 80. When positioned in the central through-hole 136 as shown in FIG. 3A, the microphone 80 is exposed to the lower subchamber 98 of the inner housing 52 and, therefore, can sense body signals S.

A certain amount of outside noise N may be conducted to the body signal microphone 80 via solid bodies such as the housings 50 and 52 and the elastomer isolators 56 and 58 that surround the microphone 80. In order to minimize the amount of this outside noise N, the microphone 80 preferably "floats" as freely as possible within the upper chamber 96 of the inner housing 52. The objective is to establish a low natural frequency structural configuration that incorporates a substantial impedance differential between the structural components that support and restrain the body signal microphone 80. In particular, the inner portion 137 of the third isolator 58 that surrounds the microphone 80 preferably makes a very soft elastomer connection with the second elastomer isolator 56 and the inner housing 52. In other words, the inner portion 137 that surrounds the microphone 80 preferably does not form a snug fit with the side and bottom walls 100 and 102 of the inner housing 52 and the upper inner surface of the second elastomer isolator.

To help achieve a soft elastomer connection, the third elastomer isolator 58 preferably has a plurality of oblong through-holes 138 evenly spaced about the circumference of the central through-hole 136. The through-holes 138 help lessen the rigidity of the third elastomer isolator 58. The lower surface 139 of the inner portion 137 preferably does not contact the bottom wall 102 of the inner housing's upper subchamber 96 so that the bottom wall 102 does not stiffen the inner portion 137 of the isolator 58 in the vertical direction. As more clearly shown in FIG. 3B, the edge 107 of the bottom wall 102 preferably is not in physical contact with the innermost edges 140 of the through-holes 138—rather, a gap is formed therebetween. As a result, the inner portion 137 of the isolator 58 is essentially suspended above the bottom surface 102.

To further help achieve a soft elastomer connection, the upper ends of the through-holes 138 are preferably at most only partially covered by the upper wall 130 of the second isolator 56. The through holes 138 in combination with the vertical and radial suspension of the inner portion 137 of the isolator 58 significantly reduces the vertical and radial stiffness of the structure that supports the body signal microphone 80. This arrangement helps the inner portion 137 of the third isolator 58 surrounding the microphone 80 to "float" more freely with respect to the remaining portion of the isolator 58, the inner housing 52, and the second isolator 56. Thus any mechanical shock or impact induced on the outer housing 50 or on the outer shield 86 will be significantly attenuated before it can be detected by the body signal microphone 80.

Preferably, the three elastomer isolators 54, 56, and 58 are of a 40 to 50 Shore A durometer and are designed to limit the level of external noise transmitted to the lower subchamber 98 of the inner housing 52.

Figure 3C:
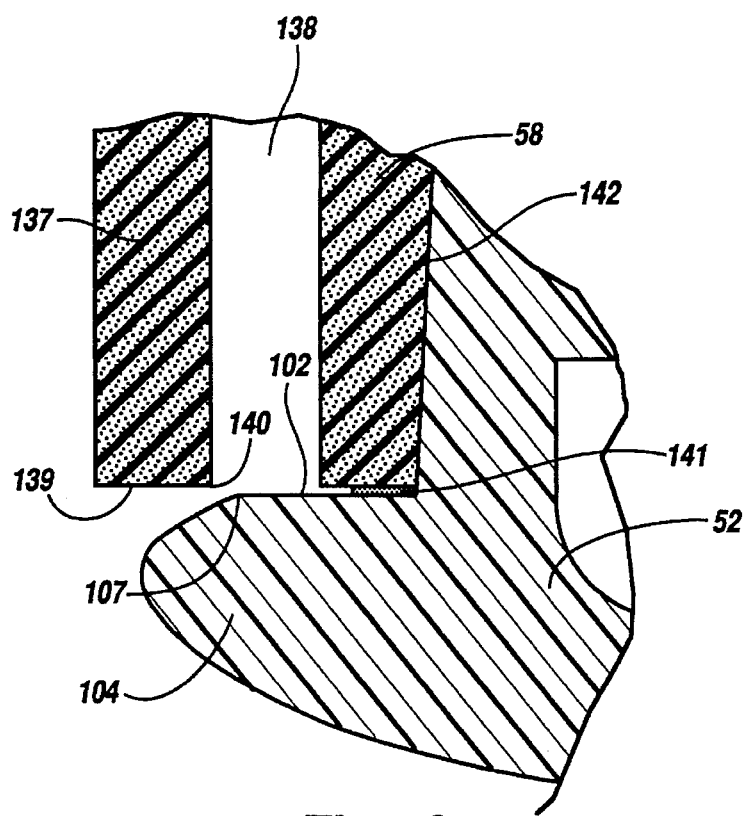
FIG. 3C is an enlarged view of a section of the transducer illustrating another variation of the invention.
Figure 4:
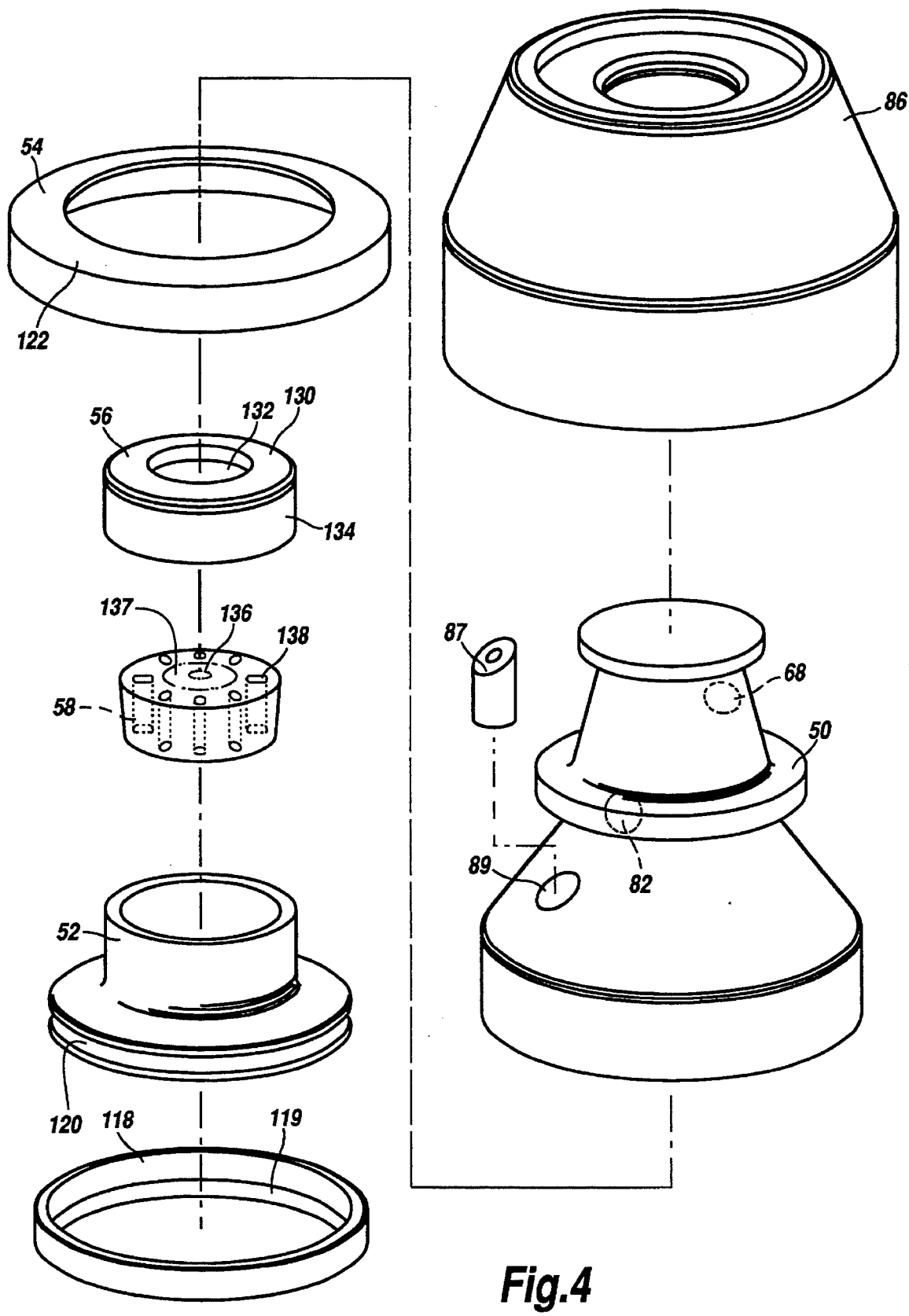
FIG. 4 is an exploded perspective view of the mechanical components of the transducer of the ASTD of FIG. 3A.

To facilitate the mechanical assembly of the inner housing, the outer side wall 142 of the third isolator 58 preferably has an approximately three degree draft or taper that matches the approximately three degree draft of the wall 100 of the inner housing's upper subchamber 96. With the use of a small shim 141 shown in FIG. 3C that is placed under the third elastomer isolator 58 (outward of the through-holes 138), the three degree draft or taper can also help space the bottom of the isolator 58 from the bottom wall 102 of the inner housing 52 and thus further aid in softening the elastomer connection discussed above.

To further limit the level of external noise transmitted to the interior of the transducer 32, the outer transducer housing 50 is preferably encapsulated by the shield 86 which may be formed from an elastomer foam. The shield 86 preferably covers the exterior of the outer housing 50 from the outer housing's lower end to the upper portion 70 of the outer housing. More or less of the outer housing 50 may be covered by the shield 86.

With the transducer 32 configured as explained above, the air chamber 93 and noise monitor microphone 88 are significantly acoustically and mechanically isolated from the lower subchamber 98 and body signal microphone 80. The body signal microphone 80 is positioned to sense sounds in the lower subchamber 98 of the inner housing 52, and the noise monitor microphone 88 is positioned to sense sounds in the air chamber 93 formed in the fourth isolator 87. Due to the sound insulating characteristics of the isolators 54, 56, and 58 and of the inner housing 52, the sounds or signals $M_{80}$ sensed by the body signal microphone 80 are primarily body signals S emanating from the patient's body (when the diaphragm 114 is placed against the patient's skin).

However, since the lower subchamber 98 of the inner housing 52 is not perfectly isolated from external sounds, the body signal microphone 80 may also sense a certain level of noise N. A significant portion of the noise N sensed by the body signal microphone 80 will be airborne noise $N_A$ that is generated by the inner surface of the inner housing 52 which can be caused by external noise that penetrates the outer shield 86, the outer housing 50 and then the inner housing 52. However, the noise may also include surface noise $N_S$ and body noise $N_B$.

With the noise monitor microphone 88 positioned away from the diaphragm 114 and surrounded by a plurality of sound barriers (the isolators 87, 54, 56 and 58, the air chamber 93, the air chamber between the inner housing and outer housing, the inner housing 52, and the outer housing 50), it is well isolated from the body signals S entering the lower subchamber 98 of the inner housing. The sounds or signals $M_{88}$ sensed by the noise monitor microphone 88, therefore, primarily are noise N that has penetrated the outer housing 50 and outer shield 86. A major portion of such noise N detected by the noise monitor microphone 88 will be airborne noise $N_A$.

As explained in more detail below, the noise monitor microphone 88 is calibrated in the absence of body signals and the resulting noise is essentially compared to the noise detected by the body signal microphone 80. Since there is a significant sound attenuating barrier between the body signal microphone 80 an the noise monitor microphone 88, the noise detected by the body signal microphone 80 will contain less energy than the noise detected by the noise monitor microphone 88. The noise detected by the noise monitor microphone 88 and defined by its wave form (frequency and amplitude) is modified and the wave form inverted and subsequently subtracted from the sound detected by the body signal microphone 80 so that only the body signals remain. The signal is then amplified and transmitted to the ears of the listener via an ear-phone/ear canal adapter, HNR headset, or HNR helmet.

Figure 5B:
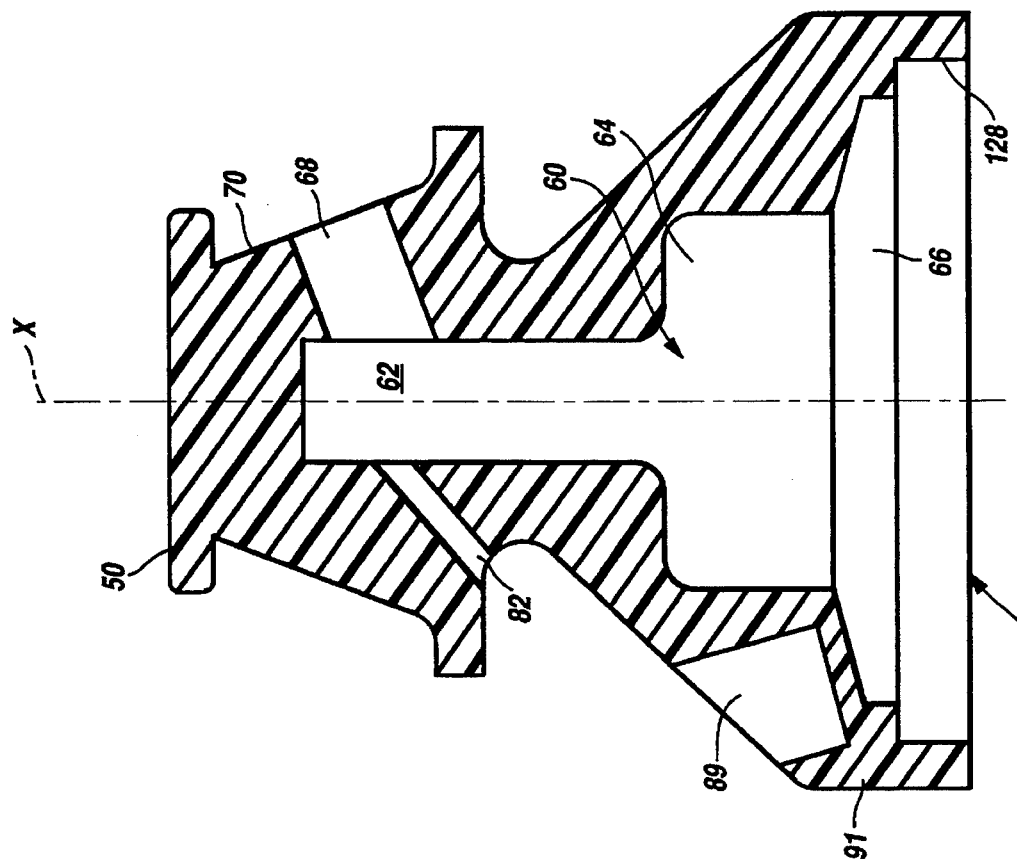
FIG. 5B is a side cross-sectional view of the outer housing of the transducer of FIG. 3D.

FIGS. 3D and 5B illustrate a second preferred embodiment of the transducer 32' forming part of the ASTD module. The transducer 32' is configured substantially the same as the transducer 32 of FIG. 3A with the exception that the outer housing 50' and fourth elastomer isolator 87' have been modified. In particular, the channel 89' of the outer housing 50' is a through hole rather than a blind hole. The channel 89' extends through the outer housing 50' to the lower subchamber 66 of the outer housing 50'. The fourth elastomer isolator 87' has been modified to have an interior cavity that closely follows the outer contour of the noise monitor microphone 88. The noise monitor microphone 88 is pressed into the interior cavity, and the fourth elastomer isolator 87' is squeezed into the channel 89'. An upper opening in the fourth elastomer isolator 87' allows passage of the second electrical conductor 78, and a lower opening exposes the noise monitor transducer 88 to the lower subchamber 66 of the outer housing 50. Preferably, the fourth isolator 87' is made from a relatively soft elastomer material that measures in the range of 40 to 50 Shore A durometer or less. Since the isolator 87' is positioned substantially within the channel 89', it has sufficient structural stability and does not need to be made from a softer elastomer material than the isolator 87 of the transducer 32 of FIG. 3A.

In the second embodiment illustrated in FIG. 3D, the noise monitor microphone 88 is positioned in or adjacent to the air chamber formed between the inner housing 52 and the outer housing 50 and away from the diaphragm 114 and lower subchamber 98 of the inner housing. The noise monitor microphone 88 is not as well isolated as the noise monitor microphone of the first embodiment illustrated in FIG. 3A. However, the microphone 88 of FIG. 3D is surrounded by a plurality of sound barriers (isolators 54, 56, 58, and 87, inner housing 52, and the outer housing 50) that isolate the noise monitor microphone 88 reasonably well from the body signals S entering the lower subchamber 98 of the inner housing. The sounds or signals $M_{88}$ sensed by the noise monitor microphone 88 will, therefore, primarily be noise N that has penetrated the outer housing 50 and outer shield 86. A major portion of such noise N detected by the noise monitor microphone 88 will be airborne noise $N_A$.

The particular embodiment of the transducer that may be more desirable depends upon the sensitivity of the noise monitor microphone 88 employed. Where the noise monitor microphone is highly sensitive, the first preferred embodiment of the transducer 32 illustrated in FIG. 3A may be more preferable since the noise monitor microphone is better isolated and would not likely detect body signals S. Where the noise monitor microphone is less sensitive, the amount of isolation provided by the transducer configuration illustrated in FIG. 3B may be sufficient to prevent the detection of body signals S by the noise monitor microphone.

With reference to FIG. 10 a block diagram of the modular auscultation and telemetry system (MASTS) is shown. FIG. 10, in particular, shows the electronic hardware contained in the waist pack 36 (represented by larger dashed lined block) that is used to condition and process signals $M_{80}$ and $M_{88}$ detected by the microphones 80 and 88 of the auscultation and telemetry device (ASTD) 31. Also shown are other modular components that may be plugged into the output receptacles 38 and, thereby electronically coupled to the electronic hardware in the waist pack 36. The plugged-in components include various receiver or speaker devices such as an ear-phone/ear-canal adapter 166, an HNR headset 40, and an HNR helmet 170, as well as a digital audio tape recorder or deck 172 and an interactive computer diagnostic trainer 174. The ear-phone/ear-canal adapter 166, HNR headset 40, and HNR helmet 170 all contain speakers 165 (shown schematically only in headset 40 and helmet 170) that emit a sound corresponding to the desired output signal $\hat{S}$ (discussed further below).

The electronic hardware contained in the waist pack 36 includes a microphone pre-amplifier 146 which is used to charge the electret condenser microphones (the body signal microphone 80 and the noise monitor microphone 88) from which the electrical sound analog signals $M_{80}$ and $M_{88}$ are derived. The electrical signals $M_{80}$ and $M_{88}$ are pre-amplified slightly and then passed through an analog high pass/low pass filter 148, where the energy within certain frequency bands in the high and low ranges is significantly attenuated in a known manner. After passing through the pre-amplifier 146 and the filter 148, the electrical signals $M_{80}$ and $M_{88}$ are converted from analog to digital signals by an analog-to-digital (A/D) converter 150 in a known manner.

The electronic hardware contained in the waist-pack 36 also includes a digital signal processor (DSP) and controller board 154 that receives the conditioned digital signals $M_{80}$ and $M_{88}$ from the analog-to-digital (A/D) converter. At the DSP 154, the conditioned digital signals $M_{80}$ and $M_{88}$ are processed to obtain the desired output signal $\hat{S}$ representing the body signal S. The DSP 154 is preferably a microprocessor having a clock speed of at least 30 to 40 megahertz so that several computations can be made on each signal sample. Such microprocessors are available from companies such as AT&T, National Instruments, and National Semiconductor. The DSP 154 and its signal processing functions are further described below with reference to FIG. 11.

From the microprocessor 154, the processed signals $\hat{S}$ are transformed back into an analog signal by a digital-to-analog (A/D) converter 162 in a known manner. The processed signals $\hat{S}$ may then be transmitted through the output receptacles 38 to a receiving device. If the signal $\hat{S}$ is being sent to a speaker device such as ear plugs 166, an HNR headset 40, or an HNR helmet 170, it preferably is first passed through a power amplifier 164 having a volume control that the user can adjust. The signal $\hat{S}$ may also be sent to a digital audio tape (DAT) recorder or tape deck 172 or an interactive computer diagnostic trainer 174 for use in diagnostic analysis or training. Where a patient's condition must be continually monitored over relatively short intervals (several minutes or hours), the processed signal $\hat{S}$ can be monitored and subsequently stored in computer memory in the computer diagnostic/trainer 174 to compare the current signal with previous signals for diagnostic purposes. This procedure promotes better health care particularly in an emergency situation. If the patient's condition must be monitored over longer periods of time (days, weeks or months), the signals $\hat{S}$ can be stored by utilizing the DAT recorder 172.

The system is powered by a battery 156 via a direct current to direct current (DC/DC) power conditioning circuit and a switch 158 that activates or deactivates the system. A memory 160 is also provided for handling the processing and to store data if desired.

As an option to ensure that the transducer 32 has been properly applied to the skin surface of the patient with sufficient pressure so that good readings can be obtained by the microphones 80 and 88, the switch 158 may be electrically connected to one or more pressure switches 176 that are mounted to the transducer 32 (see FIG. 3A). When the transducer 32 along with the pressure switches 176 are pressed against the patient's skin, the switches 176 will be activated to send a signal to activate the switch 158 within the waist-pack, which in turn activates the system. The specific positioning of the pressure switches 176 on the transducer 32 can be adjusted depending upon the amount of pressure desired or needed to be applied by the transducer 32 to ensure a good seal is formed with the patient's skin.

Figure 11A:
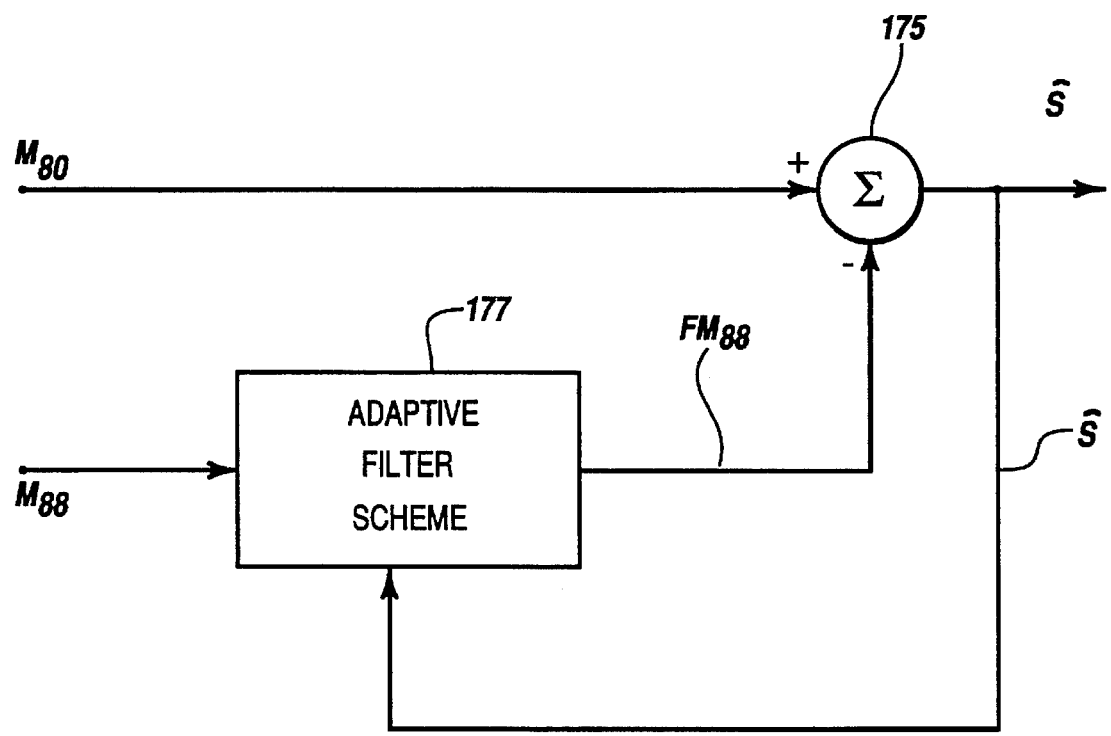
FIG. 11A is a block diagram illustrating the digital signal processing and noise cancellation performed by the digital signal processor ("DSP")
Figure 11B:
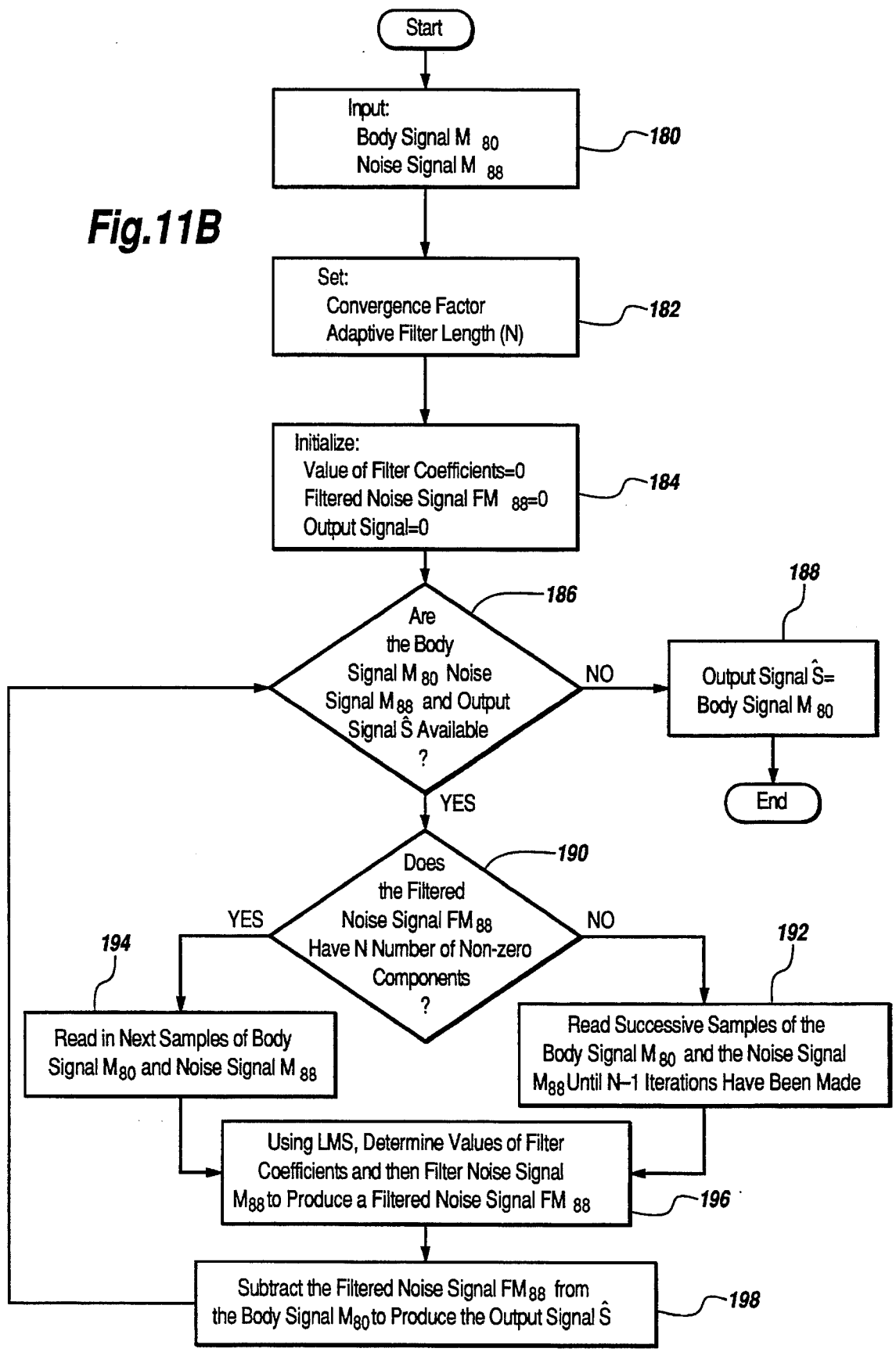
FIG. 11B is a computational flow-chart showing the steps involved in the digital signal processing and noise cancellation performed by the DSP.
Figure 14A:
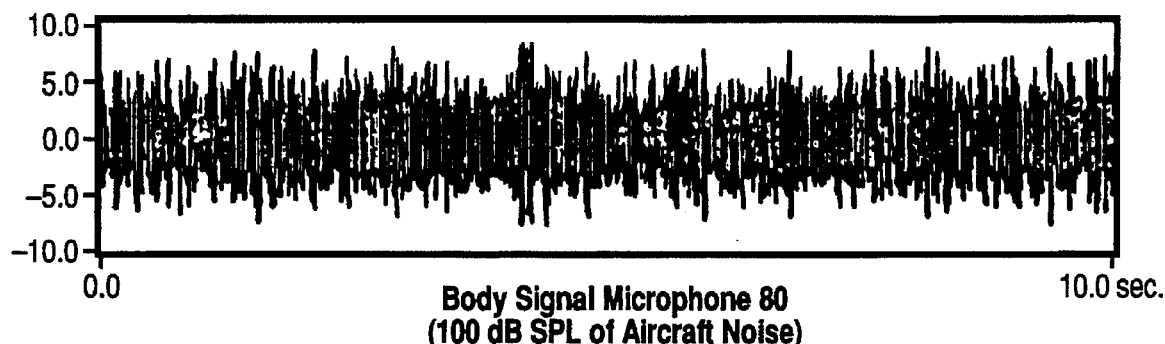
Figure 14B:
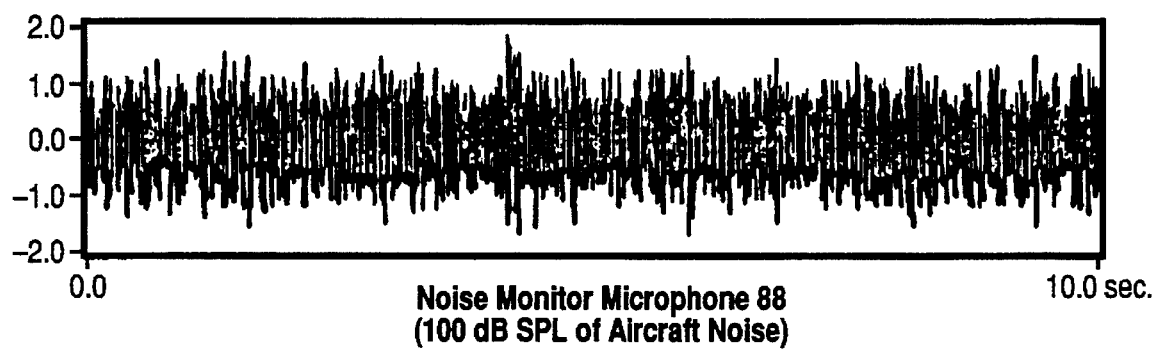
Figure 14C:
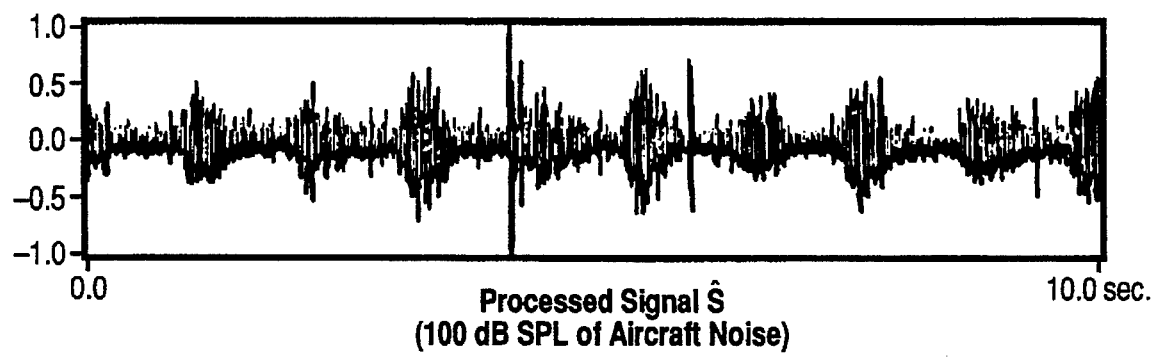

FIGS. 11A and 11B illustrate the processing function of the DSP 154. In particular, FIG. 11A illustrates a sequential block diagram of the overall signal processing functions, and FIG. 11B provides a flow chart detailing the signal processing steps. The microprocessor 154 essentially extracts the desired signal $\hat{S}$ from the input signal $M_{80}$ detected by the body signal microphone 80 by removing or cancelling unwanted noise N and distortion from the signal $M_{80}$. In addition to ambient noise $N_A$, surface motion noise $N_S$, and body noise $N_B$, such noise and distortion may include heterodynes and both white and pink noise.

The extraction is accomplished by subtracting an adaptively filtered version ($FM_{88}$) of the noise signal $M_{88}$ detected by the noise monitor microphone 88 from the body signal $M_{80}$ detected by the body signal microphone 80. The subtraction is performed by the DSP board 154 in digital form as represented by subtractor 175. As mentioned previously, the detected body signal $M_{80}$ may include noise N as well as body sounds S. The noise monitor microphone 88, however, is sufficiently isolated from the body sounds emanating from the patient that it primarily only detects noise N.

Due to the energy differences between the detected body signals $M_{80}$ and the noise signal $M_{88}$, the raw noise signal $M_{88}$, however, cannot effectively be subtracted from the body signal $M_{80}$. Therefore, the raw noise signal $M_{88}$ is first conditioned and modified by an adaptive filter scheme 177 that alters the frequency characteristics of the sampled noise signal $M_{88}$. The adaptive filter scheme preferably uses an algorithm such as a standard least mean square ("LMS") algorithm to continually alter the frequency characteristics of the sampled noise signal $M_{88}$ so that the effect of the noise signal $M_{88}$ on the body signal $M_{80}$ is minimized. The algorithm criteria (filter coefficients) are continually adapted based on the fidelity of the desired signal. A description of the LMS process can be found in the following book and article: Widrow, B. and Stearns, S. D., *Adaptive Signal Processing*, Prentice Hall, New Jersey (1985); and "Adaptive Noise Cancelling: Principles and Applications", Widrow, B. et al., *Proceedings of the IEEE*, 63(12), (1975).

With reference to FIG. 11B, and in particular box 180, the two input signals for the processing system are the digitized body signal $M_{80}$ and the noise signal $M_{88}$ each of which is input one sample at a time. Initially, as shown in box 182, a convergence factor µ and an adaptive filter length N are determined "a priori". The convergence factor µ determines how quickly the algorithm will reach a steady state condition, and the filter length N corresponds to the number of filter coefficients used by the algorithm and the number of input noise monitor signal $M_{88}$ samples used to generate the filtered noise signal $FM_{88}$. With reference to box 184 the system is initialized by setting the value of the filter coefficients and the value of the filtered noise signal $FM_{88}$ equal to zero. This results in the output signal $\hat{S}$ being initialized as equal to the body signal $M_{80}$, meaning there is no active noise cancellation.

In the next step as described in decision box 186, the system determines if the body signal $M_{80}$, the noise signal $M_{88}$, and the filtered noise signal $FM_{88}$ are available. If not, then as shown by box 188, the output signal $\hat{S}$ remains equal to the body signal $M_{80}$. If the signals are available, then the process moves to the next step where, as shown in decision box 190, it is determined whether or not the filtered noise signal $FM_{88}$ has N number of non-zero components. If the filtered noise signal $FM_{88}$ does not as yet have N number of non-zero components, then successive samples of the body signal $M_{80}$ and the noise signal $M_{88}$ are read in until N-1 iterations have been made (see box 192). Enough samples need to be taken for the algorithm to properly start working or converge and reach a steady state.

If the filtered noise signal $FM_{88}$ does have N non-zero components, then as shown by box 194, the next samples of the body signal $M_{80}$ and of the noise signal $M_{88}$ are read. Once the algorithm has reached steady state and the next samples are taken (by either taking the steps in box 192 or 194), the algorithm is used to determine the values of the filter coefficients which are then used to filter the noise signal $M_{88}$ and generate the filtered noise signal $FM_{88}$ as shown by box 196. The algorithm minimizes the effect that the noise signal has the body signal when in the next step (box 198) the filtered noise signal $FM_{88}$ is subtracted from the body signal $M_{80}$ to produce the desired output signal $\hat{S}$.

A sample of the new output signal $\hat{S}$ is then used with samples of new body and noise signals $M_{80}$ and $M_{88}$ (boxes 186, 190, 194, and 196) to determine new values of the filter coefficients and hence a new value for the filtered noise signal $FM_{88}$. The new filtered noise signal $FM_{88}$ is then subtracted from the new sample of the body signal $M_{80}$ to produce a new output signal $\hat{S}$. In this way the filter coefficients and filtered noise signal $FM_{88}$ can be adaptively adjusted based upon the knowledge of previous signal and filter coefficients.

The quality of the output signal $\hat{S}$ is greatly enhanced by the use of the digital signal processing (DSP). The signal $\hat{S}$ can be extracted from even extremely complex body signals $M_{80}$ in a fraction of a second and reproduced with little time delay. The DSP offers an increase in performance that greatly exceeds the performance of purely analog techniques. Furthermore, by using the DSP, the digitized output from the microphones 80 and 88 will be much less susceptible to electromagnetic interference that can occur in, for example, an aircraft. Other advantages of the DSP include the flexibility to be optimized for use with various body sounds in different aircraft by tuning the body signal extraction process.

FIGS. 12A–C, 13A–C, and 14A–C illustrate the results of a test using the MASTS in a simulated C-130 aircraft acoustic environment contained in a sound-proof room. Noise that was recorded on a C-130 aircraft in flight was played-back via an audio amplifier and speakers. Initially, the noise was played back so that the average sound pressure levels were 80 dB SPL in the sound-proof room. The average sound pressure levels were then increased to 90 dB SPL and 100 dB SPL. A transducer configuration similar to the transducer 32' illustrated in FIG. 3D was used in the ASTD module.

A subject was seated within the room and held the transducer against his right upper anterior chest. The subject's breathing flow rate was measured at the mouth with a pneumotachograph, and the voltages proportional to the target inspiratory and expiratory flows of 2 liters/second were marked on an oscilloscope screen to help the subject consistently meet these rates by matching the pneumotachograph output to the appropriate levels.

For each test measurement at 80, 90, and 100 dB SPL of aircraft noise, 10 seconds of acoustical and flow data was digitized at a 4,000 samples/second rate after amplification and low-pass filtering (eighth order Butterworth type) at a cutoff frequency of 1,000 Hz. The detected body sound signal $M_{80}$ from the body signal microphone 80 and the noise signal $M_{88}$ from the noise monitor microphone 88 were processed by the digital approach described with reference to FIGS. 11A and 11B. The convergence factor μ was set at 0.02, the model order was 40, and a least mean squares optimization procedure was used to determine the filter coefficients.

The body signal $M_{80}$ from the body signal microphone, the noise signal $M_{88}$, and the resultant signal $\hat{S}$ after the digital signal processing were plotted as voltages over the 10 second epoch. The signals are shown in FIGS. 12A–C for the 80 dB SPL case, in FIGS. 13A–C for the 90 dB SPL case, and in FIGS. 14A–C for the 100 dB SPL case. In each case, both inspiratory and expiratory breath sounds (roughly four of each type in each 10 second epoch) are clearly recovered (see FIGS. 12C, 13C, and 14C). Upon playback of the processed signal $\hat{S}$, the fidelity was very similar to that heard with a standard stethoscope in a quiet environment.

While several embodiments of the invention have been shown and described, it should be recognized that other variations, substitutions, or modifications will occur to those skilled in the art. Any such variations, substitutions, and modification are intended to fall within the scope of the invention as defined in the appended claims.

What is claimed is:

1. A modular auscultation sensor and telemetry system for use in sensing body sounds emanating from a living body, comprising:
    a transducer head having a first chamber and a second chamber substantially acoustically isolated from said first chamber, wherein said first chamber has an opening, said transducer head comprising
        a first sensor positioned adjacent to or in said first chamber, and
        a second sensor positioned adjacent to or in said second chamber;
    a telemetry conduit coupled to said transducer head and comprising a first signal conductor operably coupled to said first sensor and a second signal conductor operably coupled to said second sensor; and
    a signal processor operably coupled to said first and second signal conductors for receiving signals from said first and second sensors and producing an output signal that is indicative of the body sounds emanating from a living body when the transducer head is brought in contact with a living body.

2. A modular auscultation sensor and telemetry system according to claim 1, further comprising a receiver operably coupled to said signal processor.

3. A modular auscultation sensor and telemetry system according to claim 2, wherein said receiver comprises speaker means for converting the output signal from said signal processor into audible sonic waves that may heard by a user.

4. A modular auscultation sensor and telemetry system according to claim 3, wherein said speaker means comprises a hybrid noise reduction headset.

5. A modular auscultation sensor and telemetry system according to claim 2, wherein said receiver comprises a computer.

6. A modular auscultation sensor and telemetry system according to claim 1, wherein said transducer head further comprises an outer housing and an inner housing positioned within said outer housing.

7. A modular auscultation sensor and telemetry system according to claim 2, wherein said outer housing has a channel and said transducer head further comprises an isolator positioned at least partially in said channel, said isolator having an interior chamber that at least partially constitutes said second chamber.

8. A modular auscultation sensor and telemetry system according to claim 7, wherein said isolator has at least one opening connecting said interior chamber to the exterior of said isolator, and said second sensor is positioned in said opening.

9. A modular auscultation sensor and telemetry system according to claim 7, wherein said isolator comprises an elastomer material.

10. A modular auscultation sensor and telemetry system according to claim 6, wherein said inner housing is positioned within said outer housing such that a chamber is formed therebetween, and wherein said chamber at least partially constitutes said second chamber.

11. A modular auscultation sensor and telemetry system according to claim 10, wherein said outer housing is provided with a channel and an opening connecting said channel to said chamber between said inner and outer housings, and said transducer head further comprises an isolator positioned at least partially in said channel, said isolator having an interior chamber and said second sensor being at least partially positioned in said interior chamber.

12. A modular auscultation sensor and telemetry system according to claim 6, wherein said inner housing has an inner chamber that defines said first chamber and an outer opening that defines said opening to said first chamber, and wherein said transducer head further comprises at least one isolator disposed between said inner and outer housings.

13. A modular auscultation sensor and telemetry system according to claim 12, wherein said at least one isolator comprises an elastomer material.

14. A modular auscultation sensor and telemetry system according to claim 12, wherein:
    said at least one isolator includes a first isolator and a second isolator both disposed between said inner and outer housings,
    said first isolator is disposed near a first end of said inner housing and said second isolator is disposed near a second end of said inner housing, and
    said outer opening of said inner housing is located near said second end of said inner housing.

15. A modular auscultation sensor and telemetry system according to claim 14, wherein said transducer head further comprises a third isolator that at least partially surrounds said first sensor.

16. A modular auscultation sensor and telemetry system according to claim 15, wherein said third isolator has a generally wheel-like configuration with a substantially central through hole in which said sensor is at least partially received, an inner portion surrounding said central through hole, and a plurality of spoke members radiating outward from said inner portion such that spaces are formed between said spoke members.

17. A modular auscultation sensor and telemetry system according to claim 16, wherein said third isolator is positioned substantially within said inner chamber of said inner housing near said first end of said inner housing.

18. A modular auscultation sensor and telemetry system according to claim 16, wherein said third isolator is substantially positioned between a first wall of said inner housing and a first wall of said outer housing.

19. A modular auscultation sensor and telemetry system according to claim 18, wherein said first isolator is disposed at least partially between said third isolator and said first wall of said outer housing.

20. A modular auscultation sensor and telemetry system according to claim 15, wherein said transducer head further comprises a fourth isolator that at least partially surrounds said second sensor.

21. A modular auscultation sensor and telemetry system according to claim 20, wherein said outer housing has a channel and said fourth isolator is positioned at least partially within said channel.

22. A modular auscultation sensor and telemetry system according to claim 6, wherein:

said inner housing comprises first and second subchambers that are divided by a inwardly-extending protrusion of said inner housing that defines an inner opening between said first and second subchambers, said first subchamber is defined by a surface of said protrusion and a circumferential side wall of said inner housing that is at an angle to said surface of said protrusion, and said outer opening of said inner housing opens to said second subchamber; and said transducer head further comprises a first isolator that at least partially surrounds said first sensor and is disposed substantially within said first subchamber of said inner housing.

23. A modular auscultation sensor and telemetry system according to claim 22, wherein:

said first isolator has a generally wheel-like configuration with a substantially central through hole in which said first sensor is at least partially received, a plurality of outer through holes spaced radially outward from said central through hole, and an outer side wall, said central through hole and said outer through holes extending from a first end of said first isolator to a second opposing end of said first isolator.

24. A modular auscultation sensor and telemetry system according to claim 23, wherein said circumferential side wall of said inner chamber is tapered such that said first chamber increases in diameter towards said outer opening, and said outer side wall of said first isolator substantially matches the taper of said circumferential side wall and is positioned adjacent to said circumferential side wall.

25. A modular auscultation sensor and telemetry system according to claim 24, wherein said transducer head further comprises a shim disposed between said second end of said first isolator and said surface of said protrusion.

26. A modular auscultation sensor and telemetry system according to claim 22, wherein said transducer head further comprises at least one isolator disposed between said inner and outer housings.

27. A modular auscultation sensor and telemetry system according to claim 26, wherein:

said at least one isolator includes a second isolator and a third isolator both disposed between said inner and outer housing, said second isolator is disposed near a first end of said inner housing and said third isolator is disposed near a second end of said inner housing, and said outer opening of said inner housing being located near said second end of said inner housing.

28. A modular auscultation sensor and telemetry system according to claim 22, wherein said second subchamber has a generally bell-shaped configuration defined by an inner surface of said inner housing that substantially follows the contour of a segment of an inverse paraboloid, and wherein said second subchamber at least partially constitutes said first chamber.

29. A modular auscultation sensor and telemetry system according to claim 28, wherein said first sensor is substantially aligned with an axis of symmetry of said inverse paraboloid.

30. A modular auscultation sensor and telemetry system according to claim 1, wherein a portion of said first chamber near said opening substantially follows the contour of an inverse paraboloid, and said first sensor is substantially aligned with an axis of symmetry of said inverse paraboloid.

31. A modular auscultation sensor and telemetry system according to claim 1, wherein said first sensor comprises a microphone, and said second sensor comprises a microphone.

32. A modular auscultation sensor and telemetry system according to claim 1, wherein said transducer head further comprises a diaphragm that extends across said opening of said first chamber.

33. A modular auscultation sensor and telemetry system according to claim 1, wherein said transducer head further comprises a shield that at least partially surrounds said outer housing.

34. A modular auscultation sensor and telemetry system according to claim 1, further comprising a portable pack in which said signal processor is positioned.

35. A modular auscultation sensor and telemetry system according to claim 1, wherein said first conductor comprises an electrical conductor and said second conductor comprises an electrical conductor.

36. A modular auscultation sensor and telemetry system for use in sensing body sounds emanating from a living body, comprising:

a transducer head having a first chamber and a second chamber substantially isolated from said first chamber, wherein said first chamber has an opening, said transducer head comprising a first sensor positioned adjacent to or in said first chamber, a second sensor positioned adjacent to or in said second chamber, and a diaphragm that extends across said opening of said first chamber;

a telemetry conduit coupled to said transducer head and comprising a first signal conductor operably coupled to said first sensor and a second signal conductor operably coupled to said second sensor; and digital signal processing means, operably coupled to said first and second conductors for receiving signals from said first and second sensors, processing said signals and producing an output signal that is indicative of body sounds when said diaphragm of said transducer head is brought into contact with a living body.

37. A modular auscultation sensor and telemetry system according to claim 36, wherein said digital signal processing means comprises:

a microprocessor that includes an adaptive filter for processing and conditioning samples of said signals from said second sensor and generating a filtered signal, and a subtractor for subtracting said filtered signal from said signal from said first sensor to generate said output signal that is indicative of the body sounds, wherein said output signal is fed back to said adaptive filter to dynamically adjust said adaptive filter.

38. A modular auscultation sensor and telemetry system according to claim 37, wherein said digital signal processing means further comprises:

an analog-to-digital converter that transforms said signals from said first and second sensors from analog signals to digital signals; and a digital-to-analog converter that transforms said output signal from a digital signal to an analog signal.

39. A stethoscope comprising:

a transducer head having a first chamber and a second chamber substantially isolated from said first chamber, said transducer head comprising an outer housing having an inner chamber, an inner housing positioned within said inner chamber of said outer housing, said inner housing having an inner chamber that at least partially constitutes said first chamber, and an opening to said inner chamber;

a diaphragm that extends across said opening of said inner chamber, a first sensor positioned adjacent to or in said first chamber of said inner housing, and a second sensor positioned adjacent to or in said second chamber; and a telemetry conduit coupled to said transducer head comprising a first signal conductor operably coupled to said first sensor and a second signal conductor operably coupled to said second sensor.

40. A stethoscope according to claim 39, wherein:

said transducer head further comprises a first isolator and a second isolator both disposed between said inner and outer housings, said first isolator is disposed near a first end of said inner housing and said second isolator is disposed near a second end of said inner housing, and said opening of said inner housing is located near said second end of said inner housing.

41. A stethoscope according to claim 40, wherein said transducer head further comprises a third isolator that at least partially surrounds said first sensor.

42. A stethoscope according to claim 41, wherein said transducer head further comprises a fourth isolator that at least partially surrounds said second sensor.

43. A stethoscope according to claim 42, wherein said outer housing has a channel and said fourth isolator is positioned at least partially in said channel.

44. A stethoscope according to claim 43, wherein said fourth isolator has an interior chamber that at least partially constitutes said second chamber.

45. A stethoscope according to claim 43, wherein said transducer head has a chamber formed between said inner housing and said outer housing that at least partially constitutes said second chamber, and wherein said outer housing has an opening connecting said channel to said chamber between said inner and outer housings, and said fourth isolator is positioned at least partially in said channel.

* * * * *